United States Patent
Lee et al.

(10) Patent No.: US 10,188,350 B2
(45) Date of Patent: Jan. 29, 2019

(54) SENSOR DEVICE AND ELECTRONIC DEVICE HAVING THE SAME

(71) Applicant: Samsung Electronics Co., Ltd., Suwon-si, Gyeonggi-do (KR)

(72) Inventors: Seung-Hoon Lee, Seoul (KR); Min-Woo Park, Hwaseong-si (KR); Seung-Ki Choi, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 531 days.

(21) Appl. No.: 14/590,584

(22) Filed: Jan. 6, 2015

(65) Prior Publication Data

US 2015/0190094 A1 Jul. 9, 2015

Related U.S. Application Data

(60) Provisional application No. 61/924,406, filed on Jan. 7, 2014.

(30) Foreign Application Priority Data

Feb. 21, 2014 (KR) ........................ 10-2014-0020848

(51) Int. Cl.
*A61B 5/02* (2006.01)
*A61B 5/00* (2006.01)
(Continued)

(52) U.S. Cl.
CPC ........ *A61B 5/6898* (2013.01); *A61B 5/02416* (2013.01); *A61B 5/02427* (2013.01);
(Continued)

(58) Field of Classification Search
CPC .............. A61B 5/6898; A61B 5/02416; A61B 5/14551; A61B 5/742; A61B 5/0022; A61B 5/02427; A61B 5/117; A61B 2560/0462; A61B 2562/185; G06F 21/32; H04W 12/06

See application file for complete search history.

(56) References Cited

U.S. PATENT DOCUMENTS 4,163,447 A 8/1979 Orr
6,330,468 B1 12/2001 Scharf
(Continued)

FOREIGN PATENT DOCUMENTS

JP 2009-111928 A 5/2009
KR 10-2005-0103355 A 10/2005
(Continued)

*Primary Examiner* — Mallika D Fairchild
(74) *Attorney, Agent, or Firm* — Jefferson IP Law, LLP

(57) ABSTRACT

A mobile electronic device is provided. The mobile electronic device includes at least one processor, a display module electrically connected with the at least one processor, a communication module electrically connected with the at least one processor, a portable electronic device housing configured to house at least a part of the display module, the at least one processor, and the communication module, and a Heart Rate (HR) sensor (e.g., a Heart Rate Monitor (HRM) sensor) which is placed on one surface of the housing and has at least its part exposed to an outside, and which is electrically connected with the at least one processor.

12 Claims, 21 Drawing Sheets

(51) Int. Cl.
  *A61B 5/024*   (2006.01)
  *A61B 5/1455*  (2006.01)
  *A61B 5/117*   (2016.01)
  *H04W 12/06*   (2009.01)
  *G06F 21/32*   (2013.01)
  *H04W 4/80*    (2018.01)
  *H04L 29/06*   (2006.01)

(52) U.S. Cl.
  CPC .......... *A61B 5/117* (2013.01); *A61B 5/14551* (2013.01); *A61B 5/742* (2013.01); *G06F 21/32* (2013.01); *H04W 12/06* (2013.01); *A61B 5/0022* (2013.01); *A61B 2560/0462* (2013.01); *A61B 2562/185* (2013.01); *H04L 63/0861* (2013.01); *H04W 4/80* (2018.02)

(56) References Cited

U.S. PATENT DOCUMENTS

| | | |
|---|---|---|
| 6,546,232 B1 | 4/2003 | Sack et al. |
| 8,172,761 B1 | 5/2012 | Rulkov et al. |
| 2002/0151775 A1 | 10/2002 | Kondo |
| 2005/0208969 A1* | 9/2005 | Kwoen ................ A61B 5/0002 455/557 |
| 2009/0060287 A1* | 3/2009 | Hyde .................. A61B 5/0002 382/118 |
| 2010/0113950 A1 | 5/2010 | Lin et al. |
| 2011/0015496 A1 | 1/2011 | Sherman et al. |
| 2011/0065482 A1 | 3/2011 | Koide et al. |
| 2011/0150291 A1 | 6/2011 | Jung |
| 2012/0295589 A1 | 11/2012 | Alexander et al. |
| 2013/0338928 A1 | 12/2013 | Mustola et al. |
| 2014/0051941 A1* | 2/2014 | Messerschmidt .... A61B 5/6898 600/301 |
| 2014/0107493 A1* | 4/2014 | Yuen .................... H04W 4/027 600/473 |
| 2014/0313153 A1* | 10/2014 | Ootake ................ G06F 1/1692 345/173 |

FOREIGN PATENT DOCUMENTS

| | | |
|---|---|---|
| KR | 10-2006-0111159 A | 10/2006 |
| KR | 10-2009-0008170 A | 1/2009 |
| KR | 10-0880392 B1 | 1/2009 |
| KR | 10-2011-0004700 A | 1/2011 |
| WO | 2013/106607 A2 | 7/2013 |
| WO | 2013/148753 A1 | 10/2013 |

* cited by examiner

SENSOR DEVICE AND ELECTRONIC DEVICE HAVING THE SAME

CROSS-REFERENCE TO RELATED APPLICATION(S)

This application claims the benefit under 35 U.S.C. § 119(e) of a U.S. provisional patent application filed on Jan. 7, 2014 in the U.S. Patent and Trademark Office and assigned Ser. No. 61/924,406, and under 35 U.S.C. § 119(a) of a Korean patent application filed on Feb. 21, 2014 in the Korean Intellectual Property Office and assigned Serial number 10-2014-0020848, the entire disclosure of each of which is hereby incorporated by reference.

TECHNICAL FIELD

The present disclosure relates to a sensor device and an electronic device having the same. More particularly, the present disclosure relates to a sensor device which can be accommodated in an electronic device along with at least one electronic component and can reduce a mounting space and an electronic device having the same.

BACKGROUND

Electronic devices can perform various complex functions. For example, portable terminals, such as smart phones, are developing to be able to implement enhanced performance and provide much convenience to users.

Some of the functions provided by the electronic device use sensors. Such sensors may collect information on the electronic device, an outside of the electronic device, or a user.

The electronic device may be equipped with one or more sensors and provide various services by using information collected through the sensors.

Therefore, a need exists for a sensor device which can be accommodated in an electronic device along with at least one electronic component, thereby overcoming a design limit, and can reduce a mounting space, thereby improving a design of the electronic device, and an electronic device having the same.

The above information is presented as background information only to assist with an understanding of the present disclosure. No determination has been made, and no assertion is made, as to whether any of the above might be applicable as prior art with regard to the present disclosure.

SUMMARY

The electronic device may include a sensor device for recognizing user's biometric information. Related-art sensor devices have problems that they should be mounted in separate locations distinguished from those of other electronic components included in the electronic device and should be designed to be located in limited locations in order to reduce influence of other electronic components. For example, when the sensor device is mounted in a different location from those of other electronic components in the electronic device, there are problems that the thickness or length of the electronic device increases and the appearance of the electronic device is defaced. In addition, for example, an additional process or part related to the electronic device may be required and thus may increase a manufacturing cost of the electronic device.

Aspects of the present disclosure are to address at least the above-mentioned problems and/or disadvantages and to provide at least the advantages described below. Accordingly, an aspect of the present disclosure is to provide a sensor device which can be accommodated in an electronic device along with at least one electronic component, thereby overcoming a design limit, and can reduce a mounting space, thereby improving a design of the electronic device, and an electronic device having the same.

Another aspect of the present disclosure is to provide a sensor device which can improve performance of an electronic device by preventing interference between the sensor device and at least one electronic component, and an electronic device having the same.

In accordance with an aspect of the present disclosure, a mobile electronic device is provided. The mobile electronic device includes at least one processor, a display module electrically connected with the at least one processor and including a touch screen, a communication module electrically connected with the at least one processor, a portable electronic device housing configured to house at least a part of the display module, the at least one processor, and the communication module, and a Heart Rate (HR) sensor (e.g., a Heart Rate Monitor (HRM) sensor) placed on one surface of the housing and comprises at least its part exposed to an outside, and is electrically connected with the at least one processor.

In accordance with another aspect of the present disclosure, an electronic device is provided. The electronic device includes a substrate, an HR sensor mounted on the substrate, a flash Light Emitting Diode (LED) placed adjacent to the HR sensor, an integral window placed in a housing to cover the HR sensor and the flash LED all together, and a shielding unit configured to provide shielding between an area of the HR sensor and an area of the flash LED.

In accordance with another aspect of the present disclosure, a method for using an electronic device is provided. The method includes gripping, by a user, a mobile electronic device comprising a display with one hand of the user, bringing one of the user's fingers into contact with an HR sensor comprised in one surface of a housing of the mobile electronic device, and acquiring information based on data acquired by the sensor through the display of the mobile electronic device.

In accordance with another aspect of the present disclosure, a method for operating an electronic device is provided. The method includes receiving, by a mobile device comprising a housing accommodating at least a part of a display, a processor, a communication module, and an HR sensor, a user input requesting driving of an application program, detecting, by the HR sensor, a change from a part of a user's body and acquiring data, and based on at least a part of the acquired data, displaying, by the processor, information on the display through a user interface of the application program.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
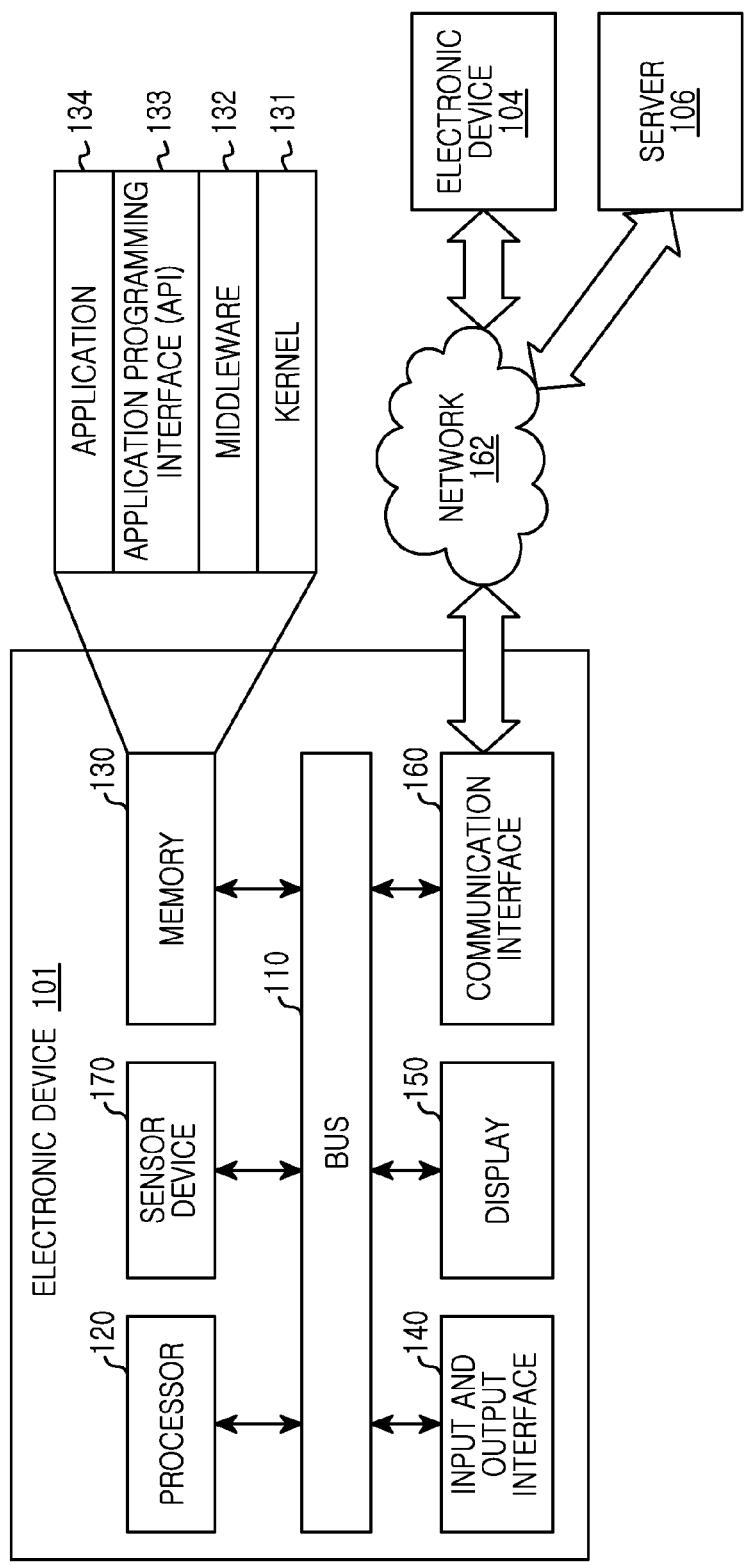
FIG. 1 illustrates a network environment including an electronic device according to various embodiments of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Although the terms, such as "first" and "second", used in the various embodiments of the present disclosure may modify various elements of the various embodiments, these terms do not limit the corresponding elements. For example, these terms do not limit an order and/or importance of the corresponding elements. These terms may be used for the purpose of distinguishing one element from another element. For example, a first user device and a second user device all indicate user devices and may indicate different user devices. For example, a first element may be named a second element without departing from the scope of right of the various embodiments of the present disclosure, and similarly, a second element may be named a first element.

It will be understood that when an element is "connected" or "coupled" to another element, the element may be directly connected or coupled to another element, and there may be an intervening element between the element and another element. To the contrary, it will be understood that when an element is "directly connected" or "directly coupled" to another element, there is no intervening element between the element and another element.

The terms used in the various embodiments of the present disclosure are for the purpose of describing particular embodiments and are not intended to limit the present disclosure. As used herein, the singular forms are intended to include the plural forms as well, unless the context clearly indicates otherwise.

All of the terms used herein including technical or scientific terms have the same meanings as those generally understood by an ordinary skilled person in the related art unless they are defined otherwise. The terms defined in a generally used dictionary should be interpreted as having the same meanings as the contextual meanings of the relevant technology and should not be interpreted as having ideal or exaggerated meanings unless they are clearly defined in the various embodiments of the present disclosure.

An electronic device according to various embodiments of the present disclosure may be a device that includes a sensor device. For example, the electronic device may include at least one of a smartphone, a tablet personal computer (PC), a mobile phone, a video phone, an electronic book reader, a desktop PC, a laptop PC, a netbook computer, a Personal Digital Assistant (PDA), a Portable Multimedia Player (PMP), a Motion Pictures Expert Group (MPEG-1 or MPEG-2) Audio Layer 3 (MP3) player, a mobile medical machine, a camera, or a wearable device (e.g., a head-mounted-device (HMD), such as electronic glasses, electronic clothing, an electronic bracelet, an electronic necklace, an electronic appccessory, electronic tattoos, a smartwatch, and the like).

According to an embodiment of the present disclosure, the electronic device may be a smart home appliance that is equipped with a function of detecting an external environment or biometric information. For example, the smart home appliance may include at least one of a television, a Digital Video Disk (DVD) player, a stereo, a refrigerator, an air conditioner, a cleaner, an oven, a microwave oven, a washing machine, an air cleaner, a set-top box, a Television (TV) box (for example, Samsung HomeSync™, Apple TV™, or Goggle TV™), a game console, an electronic dictionary, an electronic key, a camcorder, or an electronic album.

According to an embodiment of the present disclosure, the electronic device may include at least one of various medical machines (for example, Magnetic Resonance Angiography (MRA), Magnetic Resonance Imaging (MRI), Computerized Tomography (CT), a tomograph, an ultrasound machine, and the like), a navigation device, a Global Positioning System (GPS) receiver, an Event Data Recorder (EDR), a Flight Data Recorder (FDR), an automotive infotainment device, an electronic equipment for ship (for example, a navigation equipment for ship, a gyro compass, and the like), avionics, a security device, a head unit for vehicle, an industrial or home robot, an Automatic Teller's Machine (ATM) of a financial institution, a Point of Sales (POS) of a store, and the like.

According to an embodiment of the present disclosure, the electronic device may include at least one of a part of furniture or a building/a structure including a sensor device, an electronic board, an electronic signature receiving device, a projector, and various measurement devices (for example, water, power, gas, radio waves, and the like). The electronic device according to various embodiments of the present disclosure may be a combination of one or more of the above-mentioned devices. In addition, it is obvious to an ordinary skilled person in the related art that the electronic device according to various embodiments of the present disclosure is not limited to the above-mentioned devices.

Hereinafter, an electronic device according to various embodiments of the present disclosure will be described with reference to the accompanying drawings. The term "user" used in various embodiments of the present disclosure may refer to a person who uses the electronic device or a device that uses the electronic device (for example, an artificial intelligence electronic device).

FIG. 1 illustrates a network environment including an electronic device according to various embodiments of the present disclosure.

Referring to FIG. 1, an electronic device 101 may include a bus 110, a processor 120, a memory 130, an input and output interface 140, a display 150, a communication interface 160, and a sensor device 170.

The bus 110 may be a circuit which connects the above-described elements with one another and transmits communication (e.g., a control message) between the above-described elements.

The processor 120 may receive instructions from the other elements (e.g., the memory 130, the input and output interface 140, the display 150, the communication interface 160, and the like) via the bus 110, decipher the instructions, and perform calculation or data processing according to the deciphered instructions.

The memory 130 may store instructions or data which is received from or generated by the processor 120 or the other elements (e.g., the input and output interface 140, the display 150, the communication interface 160, and the like). For example, the memory 130 may include programming modules, such as a kernel 131, middleware 132, an Application Programming Interface (API) 133, an application 134, and the like. Each of the above-described programming modules may be configured by software, firmware, hardware, or a combination of two or more of them.

The kernel 131 may control or manage system resources (e.g., the bus 110, the processor 120, the memory 130, and the like) which are used for performing operations or functions implemented in the other programming modules, for example, the middleware 132, the API 133, or the application 134. In addition, the kernel 131 may provide an interface for allowing the middleware 132, the API 133, or the application 134 to access an individual element of the electronic device 101 and control or manage the element.

The middleware 132 may serve as an intermediary to allow the API 133 or the application 134 to communicate with the kernel 131 and exchange data with the kernel 131. In addition, the middleware 132 may perform controlling (e.g., scheduling or load balancing) with respect to work requests received from the application 134, for example, by giving priority to use the system resources of the electronic device 101 (e.g., the bus 110, the processor 120, the memory 130, and the like) to at least one of the applications 134.

The API 133 is an interface for allowing the application 134 to control a function provided by the kernel 131 or the middleware 134, and, for example, may include at least one interface or function (e.g., instructions) for controlling a file, for controlling a window, for processing an image, for controlling a text, and the like.

According to various embodiments of the present disclosure, the application 134 may include a Short Message Service (SMS)/Multimedia Messaging Service (MMS) application, an email application, a calendar application, a notification application, a health care application (e.g., an application for measuring exercise or a blood sugar), an environment information application (e.g., an application for providing information on atmospheric pressure, humidity, or temperature), and the like. Additionally or alternatively, the application 134 may be an application related to information exchange between the electronic device 101 and an external electronic device (e.g., an electronic device 140). For example, the application related to the information exchange may include a notification relay application for relaying specific information to the external electronic device or a device management application for managing the external electronic device.

For example, the notification relay application may include a function of relaying notification information generated by other applications of the electronic device 101 (e.g., the SMS/MMS application, the email application, the health care application, the environment information application, and the like) to the external electronic device (e.g., the electronic device 104). Additionally or alternatively, the notification relay application may receive notification information from the external electronic device (e.g., the electronic device 104) and may relay the same to the user. For example, the device management application may manage (e.g., install, delete or update) a function regarding at least part of the external electronic device (e.g., the electronic device 104) communicating with the electronic device 101 (e.g., turning on/off the external electronic device (or some parts) or adjusting brightness of a display), an application operating in the external electronic device or a service provided by the external electronic device (e.g., a calling service or a message service).

According to various embodiments of the present disclosure, the application 134 may include an application specified according to an attribute (e.g., a kind of an electronic device) of the external electronic device (e.g., the electronic device 104). For example, when the external electronic device is an MP3 player, the application 134 may include an application related to music replay. Similarly, when the external electronic device is a mobile medical device, the application 134 may include an application related to health care. According to an embodiment of the present disclosure, the application 134 may include at least one of an application specified by the electronic device 101 or an application received from the external electronic device (e.g., a server 106 or the electronic device 104).

The input and output interface 140 may transmit instructions or data input by the user through an input and output device (e.g., a sensor, a keyboard, a touch screen, and the like) to the processor 120, the memory 130, or the communication interface 160 through the bus 110, for example. For example, the input and output interface 140 may provide data on a user's touch input through a touch screen to the processor 120. In addition, the input and output interface 140 may output instructions or data received from the processor 120, the memory 130, or the communication interface 160 through the bus 110 through the input and output device (e.g., a speaker or a display). For example, the input and output interface 140 may output audio data processed by the processor 120 to the user through a speaker.

The display 150 may display a variety of information (e.g., multimedia data, text data, and the like) for the user.

The communication interface 160 may connect communication between the electronic device 101 and the external device (e.g., the electronic device 104 or the server 106). For example, the communication interface 160 is connected to a network 162 via wireless communication or wire communication to communicate with the external device. The wireless communication may include at least one of Wireless Fidelity (WiFi), Bluetooth (BT), Near Field Communication (NFC), Global Positioning System (GPS), or cellular communication (e.g., Long Term Evolution (LTE), LTE-Advanced (LTE-A), Code Division Multiple Access (CDMA), Wideband CDMA (WCDMA), Universal Mobile Telecommunications System (UMTS), Wireless Broadband (WiBro), Global System for Mobile Communications (GSM), and the like). The wire communication may include at least one of a Universal Serial Bus (USB), a High Definition Multimedia Interface (HDMI), a Recommended Standard 232 (RS-232), a Plain Old Telephone Service (POTS), and the like.

According to an embodiment of the present disclosure, the network 162 may be a telecommunications network. The telecommunications network may include at least one of a computer network, the Internet, Internet of things, a telephone network, and the like. According to an embodiment of the present disclosure, a protocol for communicating between the electronic device 101 and the external device (e.g., a transport layer protocol, a data link layer protocol or a physical layer protocol) may be supported in at least one of the application 134, the application programming interface 133, the middleware 132, the kernel 131, or the communication interface 160.

The sensor device 170 may acquire external environment information of the electronic device 101 or biometric information. For example, the electronic device 101 may detect at least one of humidity, temperature, heat, illumination, light, ion, vibration, radiation, sound waves, ultrasonic waves, pressure, a chemical component, a biological reaction, and the like, through the sensor device 170. In addition, for example, the electronic device 101 may detect at least one of a heart rate, a body resistance, a fingerprint, iris, brain waves, a face, blood pressure, a posture through the sensor device 170, and the like.

A Heart Rate (HR) sensor (e.g., Heart Rate Monitor (HRM) sensor) to be applied to the electronic device will be illustrated to describe various embodiments of the present disclosure. The HR sensor may detect a heart rate of a user of the electronic device. Embodiments of the present disclosure are not limited to the HR sensor and may be applied to various sensors for biometric recognition. According to an embodiment of the present disclosure, the sensor device may include various sensors, such as a facial recognition sensor for recognizing an identity of a person, an iris recognition sensor, a finger print recognition sensor, and the like. According to an embodiment of the present disclosure, the sensor device may include various medical sensors for detecting a body state of a person. According to an embodiment of the present disclosure, the electronic device may include at least one of the above-described sensors.

Figure 2A:
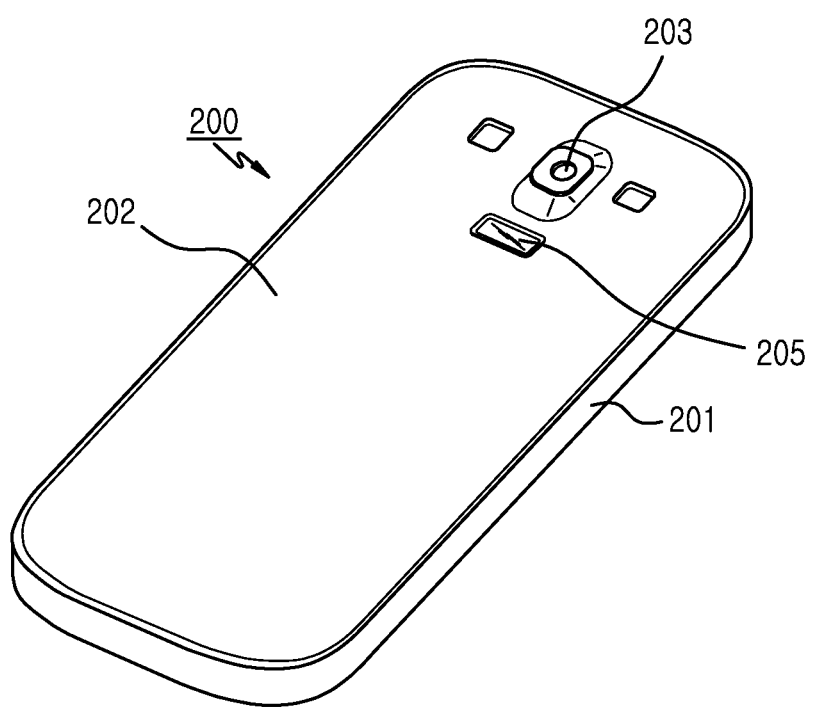
FIG. 2A illustrates a rear perspective view of an electronic device where a heart rate (HR) sensor device is placed according to various embodiments of the present disclosure.

FIG. 2A illustrates a rear perspective view of an electronic device where an HR sensor device is placed according to various embodiments of the present disclosure. For example, an electronic device 200 according to an embodiment of the present disclosure may be the electronic device 101 shown in FIG. 1. For example, an HR sensor device 205 according to an embodiment of the present disclosure may be the sensor device 170 shown in FIG. 1.

Referring to FIG. 2A, the electronic device 200 may include the HR sensor device 205 which is placed on one surface of the electronic device 200 (e.g., a rear surface 202). According to an embodiment of the present disclosure, the HR sensor device 205 may measure a pulse, a heart rate, or oxygen saturation of a user of the electronic device. According to an embodiment of the present disclosure, the HR sensor device 205 may detect the user's pulse or oxygen saturation by allowing light to pass through or reflect from a human blood vessel by using a Light Emitting Diode (LED) or an Infrared Ray (IR) LED and detecting returning light as a current by using a photo detector or a photo diode. According to an embodiment of the present disclosure, the HR sensor device 205 may measure a blood flow rate by allowing light to reflect from or pass through a blood vessel of a skin.

The embodiment of the present disclosure illustrates and discloses the HR sensor device 205 but is not limited to this and may use various kinds of biometric information measuring sensor devices.

According to various embodiments of the present disclosure, the HR sensor device 205 may be placed on an appropriate location of a rear surface of the electronic device 200. According to an embodiment of the present disclosure, the HR sensor device may be located away from a border of the electronic device 200 by a specified distance. According to an embodiment of the present disclosure, the HR sensor device 205 may be placed adjacent to another electronic component (e.g., a camera device 203) placed on the rear surface 202 of the electronic device 200. According to an embodiment of the present disclosure, the HR sensor device 205 may be placed such that its part is exposed to the outside of an external housing 201 of the electronic device 200. Therefore, when the user grips the electronic device 200, a user's finger (e.g., an index finger) is in contact with the HR sensor device 205 in the most comfortable state. According to an embodiment of the present disclosure, the HR sensor device 205 may be connected with another element of the electronic device 200 which is exposed to the outside of the external housing 201 and is not included in the HR sensor device 205 and may acquire biometric information.

Figure 2B:
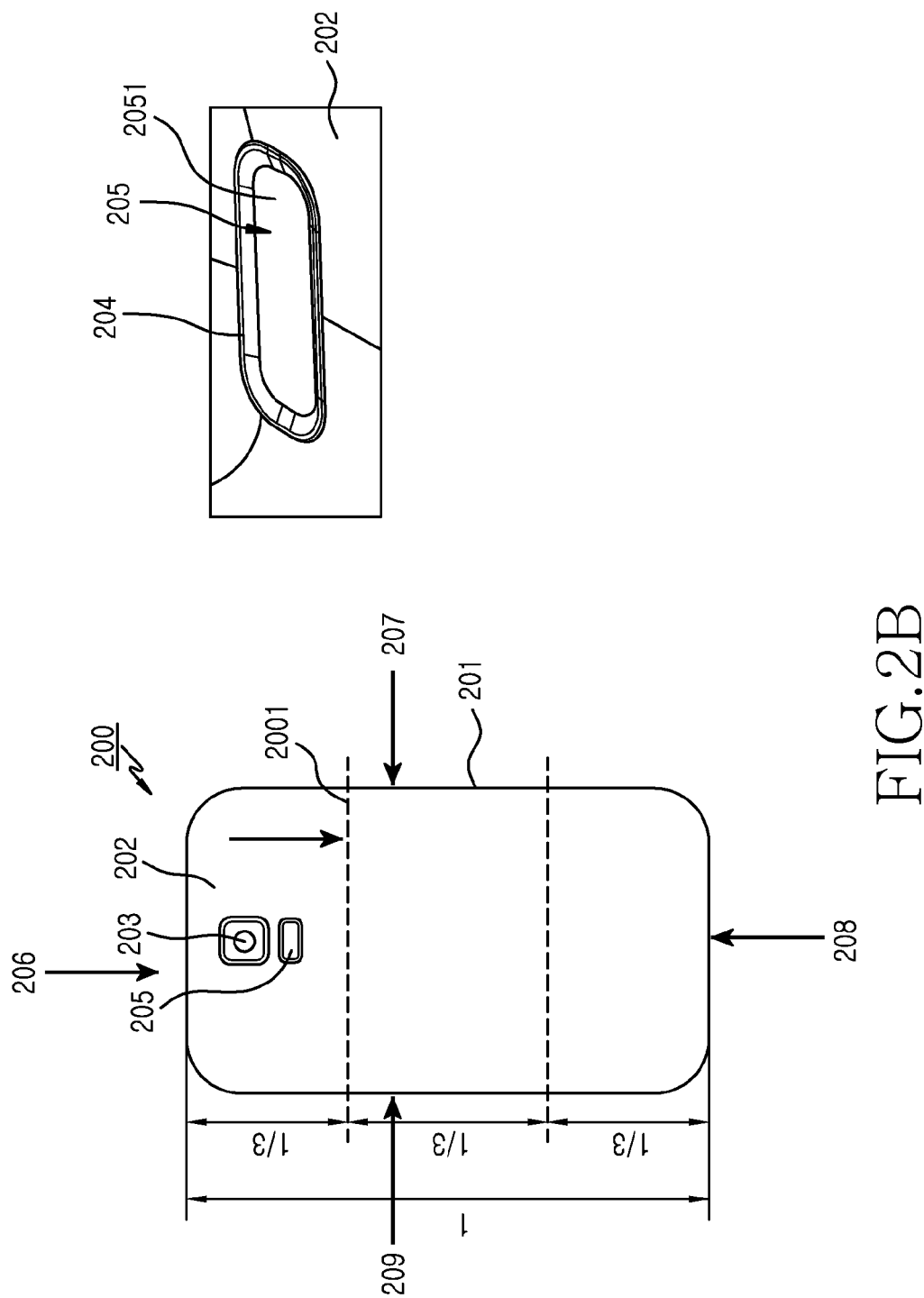
FIG. 2B illustrates a rear plane view of an electronic device where an HR sensor device is placed according to various embodiments of the present disclosure.

FIG. 2B illustrates a rear plane view of an electronic device where an HR sensor device is placed according to various embodiments of the present disclosure.

Referring to FIG. 2B, the short side located on the uppermost end of the electronic device 200 when being viewed from the rear of the electronic device 200 is referred to as a first side 206, and the side longer than the first side and perpendicular to the first side is referred to as a second side 207.

The side having the same length as that of the first side and parallel to the first side is referred to as a third side 208, and the side having the same length as that of the second side and parallel to the second side is referred to as a fourth side 209.

Referring to FIG. 2B, the HR sensor device 205 may be placed between an imaginary line 2001 which crosses over a ⅓ point of the length of the second side from the first side and the first side when being viewed from the rear of the electronic device 200.

However, this should not be considered as limiting. The HR sensor device 205 may be placed on a location such that the user's finger (e.g., an index finger) can be in contact with the HR sensor device 205 in a comfortable state when the user grips the electronic device 200 according to a size or shape of the electronic device 200.

According to an embodiment of the present disclosure, the area reachable by the user's finger may be located close to the left or right border with reference to a center point of the electronic device 200. For example, in the case of a tablet computer, a sensor device (e.g., the HR sensor device 205) may be placed on a location such that, when the user grips the tablet computer with at least one of the user's both hands, the user naturally brings his/her finger into contact with the sensor device while holding the tablet computer with the user's hand. For example, a plurality of sensor devices may be placed on locations such that the user naturally brings his/her fingers of the left or right hand into contact with the sensor devices while gripping the electronic device. For example, a plurality of sensor devices corresponding to user's left or right hand may recognize different information. For example, the sensor device corresponding to the user's left hand may be related to an authentication function and thus recognize a user's fingerprint. For example, the sensor device corresponding to the user's right hand may be related to a health care function and thus recognize a user's heart rate and the like.

According to an embodiment of the present disclosure, the HR sensor device 205 may be placed in the electronic device 200 and have its part exposed to the outside of the electronic device 200 through the external housing 201. According to an embodiment of the present disclosure, a sensor window 2051 of the HR sensor device 205 may be exposed to the outside of the electronic device 200 through the external housing 201. According to an embodiment of the present disclosure, a surface of the sensor window 2051 may serve as a part that the user's finger is brought into contact with. According to an embodiment of the present disclosure, the sensor window 2051 may be supported by a decoration member 204 which may coincide with the surface of the external housing 201 or may further protrude than the external housing 201. However, the surface of the sensor window 2051 may be located lower than the external surface of the external housing 201. According to an embodiment of the present disclosure, the surface of the sensor window 2051 may coincide with the surface of the external housing 201 of the electronic device 200.

Figure 2C:
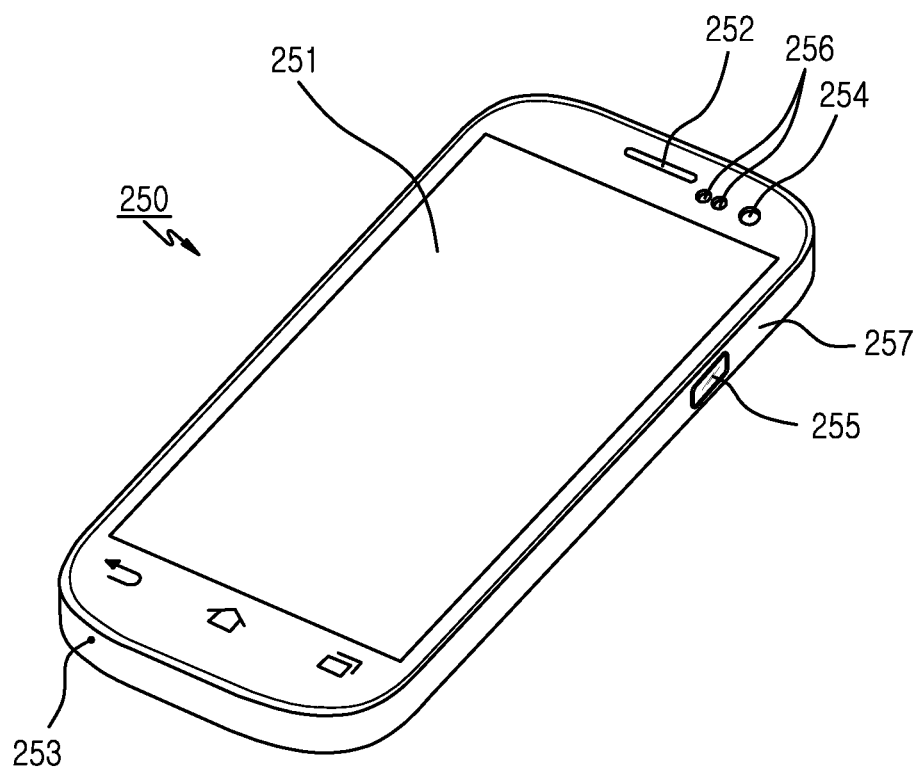
FIG. 2C illustrates a front perspective view of an electronic device where an HR sensor device is placed according to various embodiments of the present disclosure.

FIG. 2C illustrates a front perspective view of an electronic device where an HR sensor device is placed according to various embodiments of the present disclosure. According to an embodiment of the present disclosure, an electronic device 250 may be the electronic device 101 shown in FIG. 1, for example. According to an embodiment of the present disclosure, an HR sensor device 255 may be the sensor device 170 shown in FIG. 1, for example.

Referring to FIG. 2C, the electronic device 250 may include a display 251, a speaker device 252, a microphone device 253, and the like. According to an embodiment of the present disclosure, the electronic device 250 may include a touch sensor for detecting an external object in contact with or approaching at least a part of the electronic device 250. For example, the touch sensor may be a touch screen which is optically transparent and is provided on a front portion or a rear portion of the display 251. For example, the touch sensor may be integrated into the display 251.

According to an embodiment of the present disclosure, components for performing various functions of the electronic device 250 may be placed around the speaker device 252. According to an embodiment of the present disclosure, a camera device 254 may be placed on the front surface of the electronic device 250. For example, the camera device 254 may include an image sensor for detecting light of a visible area or an invisible area. The image sensor may photograph a subject located outside of the electronic device 250 or may detect a motion of another object located outside of the electronic device 250. In addition, at least one sensor module 256 may be placed to operate the electronic device 250 variably according to a surrounding environment. The sensor module 256 may include an illumination sensor for detecting ambient illumination and automatically adjusting brightness of the display 251 according to the detected illumination value, and/or a proximity sensor for detecting the electronic device being attached to a head portion of the user while the user is on the phone and inactivating the display 251. According to an embodiment of the present disclosure, although not shown, the electronic device 250 may further include at least one LED indicator which is placed at one side of the electronic device 250 and notifies the user of various states of the electronic device 250.

According to an embodiment of the present disclosure, the HR sensor device 255 may be placed on a side surface 257 of the electronic device 250. In this case, the HR sensor device 255 may be placed on a specified location of the side surface 257 such that, when the user grips the electronic device 250 with his/her right hand, the user's thumb is easily brought into contact with the HR sensor device 255. According to an embodiment of the present disclosure, the HR sensor device 255 may be placed on a specified location of the side surface 257 such that, when the user grips the electronic device 250 with his/her left hand, the user's index finger or middle finger is most comfortably brought into contact with the HR sensor device 255. However, this should not be considered as limiting and the HR sensor device 255 may be placed on a location (i.e., an upper side surface, a lower side surface, or a left or right side surface of the electronic device) such that, when the user grips the electronic device 200 according to a size or shape of the electronic device 200, the user's finger (e.g., a thumb, an index finger, a middle finger, and the like) is brought into contact with the HR sensor device 255 in a most comfortable state.

According to an embodiment of the present disclosure, a plurality of HR sensor devices 255 may be placed on various locations of the electronic device 250. For example, one HR sensor device 205 may be placed on the rear surface of the electronic device 200 as shown in FIG. 2A, and additionally or alternatively, an HR sensor device may be placed on the side surface 257 of the electronic device 250 as shown in FIG. 2C. In this case, the HR sensor devices 205 and 255 may be driven when the finger (e.g., the index finger or thumb) of the user gripping the electronic device 200 or the electronic device 250 is brought into contact with the HR sensor devices. According to an embodiment of the present disclosure, the electronic device 200 or the electronic device 250 may drive both the two HR sensor devices 205 and 255 and receive biometric recognition information acquired by the two HR sensor devices 205 and 255, and may improve biometric information recognition performance based on the biometric recognition information. For example, the electronic device may calculate more precise biometric recognition information by applying a weight to biometric recognition information acquired by the HR sensor devices 205 and 255 or calculating an average. In an embodiment of the present disclosure, the plurality of HR sensor devices are illustrated, but this should not be considered as limiting. For example, each of the plurality of sensor devices may recognize different biometric information and may provide various functions to the user by using the biometric information.

Figure 3:
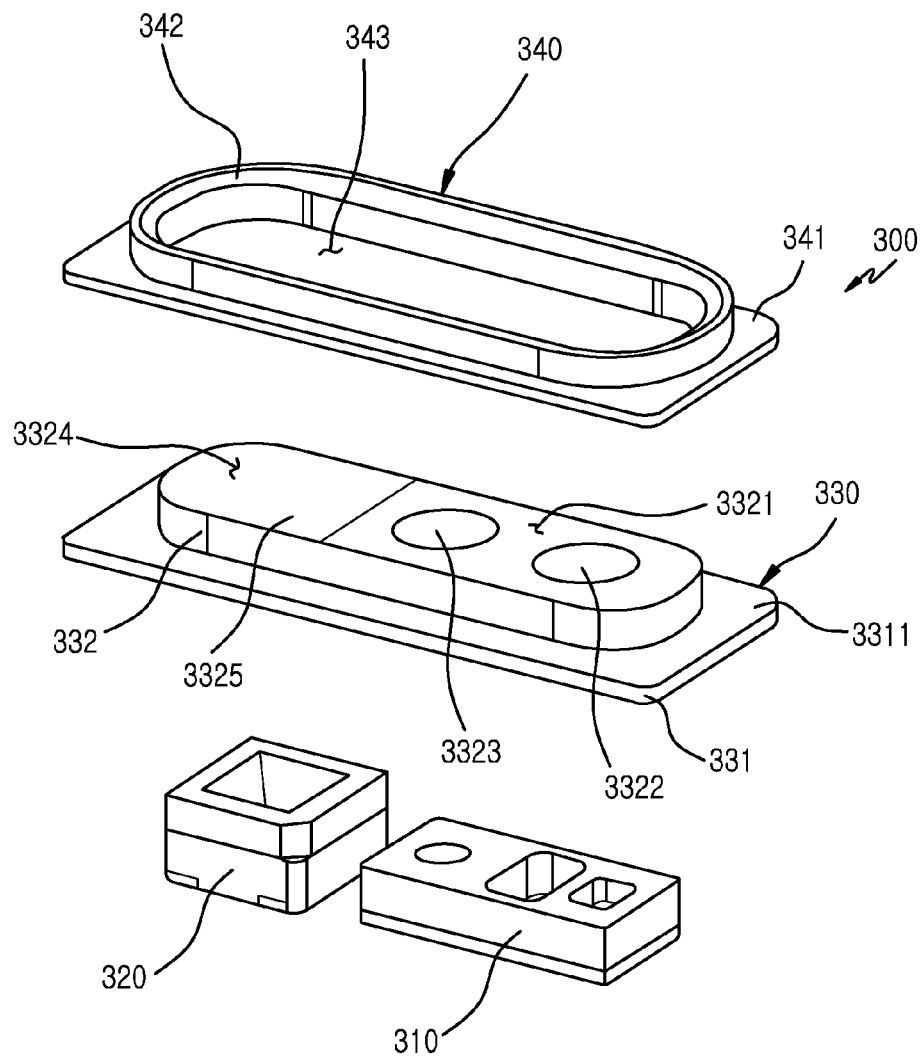
FIG. 3 illustrates an exploded front perspective view of an HR sensor device according to various embodiments of the present disclosure.

FIG. 3 illustrates an exploded front perspective view of an HR sensor device according to various embodiments of the present disclosure. An HR sensor device 300 according to an embodiment of the present disclosure may be the HR sensor device 205 or 255 shown in FIGS. 2A, 2B, and 2C.

In an embodiment of the present disclosure, the HR sensor device 300 including a flash LED 320 as an electronic component to be applied along with an HR sensor 310 (e.g., an HRM sensor) is illustrated and described. However, this should not be considered as limiting. For example, instead of the HR sensor 310, other biometric recognition sensors may be applied and at least one other electronic component may be applied in addition to the flash LED 320.

Referring to FIG. 3, the HR sensor device 300 may include the HR sensor 310 and the flash LED 320 which are arranged parallel with each other in the electronic device. According to an embodiment of the present disclosure, a window 330 is placed over the HR sensor 310 and the flash LED 320 and an instrument (e.g., a decoration member 340) for supporting the window 330 may be placed on the top of the window 330. The instrument (e.g., the decoration member 340) may be designed to have a shape to make it easy to seat the user's finger or improve the appearance of the electronic device for aesthetic purpose.

According to an embodiment of the present disclosure, the window 330 may have a size to cover the HR sensor 310 and the flash LED 320 simultaneously. According to an embodiment of the present disclosure, the window 330 may include a plate 331 of a specified area and a first protrusion 332 protruding from a first surface 3311 of the plate 331. The first protrusion 332 is coupled to the decoration member 340 by being seated on the decoration member 340 through an opening 343 of the decoration member 340, such that a flash area 3324 and an HR sensor area 3321 of the first protrusion 332 are exposed to the outside of the external housing of the electronic device.

According to an embodiment of the present disclosure, the first protrusion 332 may be integrally formed with the flash area 3324 and the HR sensor area 3321. Herein, the flash area 3324 vertically overlaps with the flash LED 320 and the HR sensor area 3321 vertically overlaps with the HR sensor 310. According to an embodiment of the present disclosure, the flash area 3324 may include a flash waveguide portion 3325 to guide light emitted from the flash LED 320 to the outside. According to an embodiment of the present disclosure, the HR sensor area 3321 may include a light emitting waveguide portion 3322 to guide infrared rays emitted from an IR LED included in the HR sensor 310, and a light receiving waveguide portion 3323 corresponding to a light receiving portion which receives infrared rays reflected from the user's finger and detects the infrared rays. According to an embodiment of the present disclosure, at least the flash waveguide portion 3325, the light emitting waveguide portion 3322, and the light receiving waveguide 3323 of the window 330 may be optically transparent.

According to various embodiments of the present disclosure, the decoration member 340 may include a flange 341 fixed to the external housing of the electronic device, and an exposure portion 342 protruding from the flange 341 and exposed to the outside of the external housing of the electronic device. According to an embodiment of the present disclosure, the decoration member 340 may have the opening 343 to accommodate the first protrusion 332 of the window 330, and the exposure portion 342 may protrude along an edge of the opening 343. According to an embodiment of the present disclosure, since the decoration member 340 is placed to be exposed to the outside of the external housing of the electronic device, the decoration member 340 may be made from materials which can make the appearance of the electronic device good, such as metal, plated synthetic resin, and the like.

Figure 4:
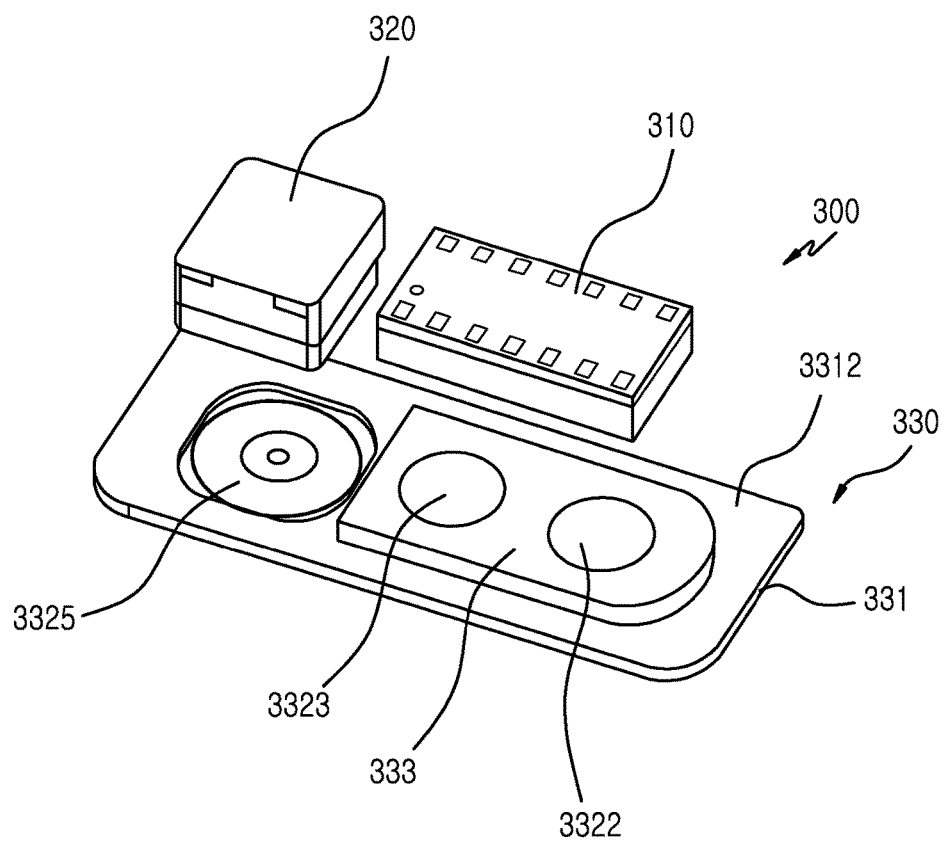
FIG. 4 illustrates an exploded rear perspective view of an HR sensor device according to various embodiments of the present disclosure.

FIG. 4 illustrates an exploded rear perspective view of an HR sensor device according to various embodiments of the present disclosure.

Referring to FIG. 4, a second surface 3312 of the window 330 may include a second protrusion 333 protruding from the plate 331 to a specified height. According to an embodiment of the present disclosure, the second protrusion 333 may be formed on an area which vertically overlaps with the HR sensor 310. Accordingly, the second protrusion 333 may accommodate the light emitting waveguide portion 3322 and the light receiving waveguide portion 3323.

According to various embodiments of the present disclosure, the window 330 may be formed to accommodate the HR sensor 310 and the flash LED 320, which perform different operations, all together. According to an embodiment of the present disclosure, the window 330 may further include a shielding unit for preventing interference between the HR sensor 310 and the flash LED 320 which perform different operations. According to an embodiment of the present disclosure, to implement the shielding unit, the top surface of the second protrusion 333 except for the areas of the light emitting waveguide portion 3322 and the light receiving waveguide portion 3323 may be black printed. According to an embodiment of the present disclosure, the top surface of the second protrusion 333 except for the areas of the light emitting waveguide portion 3322 and the light receiving waveguide portion 3323 may be mirroring-treated. According to an embodiment of the present disclosure, light emitted from the flash LED 320 may be prevented from entering the light emitting waveguide portion 3322 or the light receiving waveguide portion 3323 of the HR sensor 310 by the black printed top surface of the second protrusion 333. According to an embodiment of the present disclosure, the performance of the HR sensor 310 may not deteriorate in relation to the operation of the flash LED 320 by the above-described light shielding structure of the window 330. The light shielding structure may improve the performance of the HR sensor device 300 by reducing an amount of loss of infrared rays output from the light emitting waveguide portion 3322 and arriving at an external object.

Figure 5:
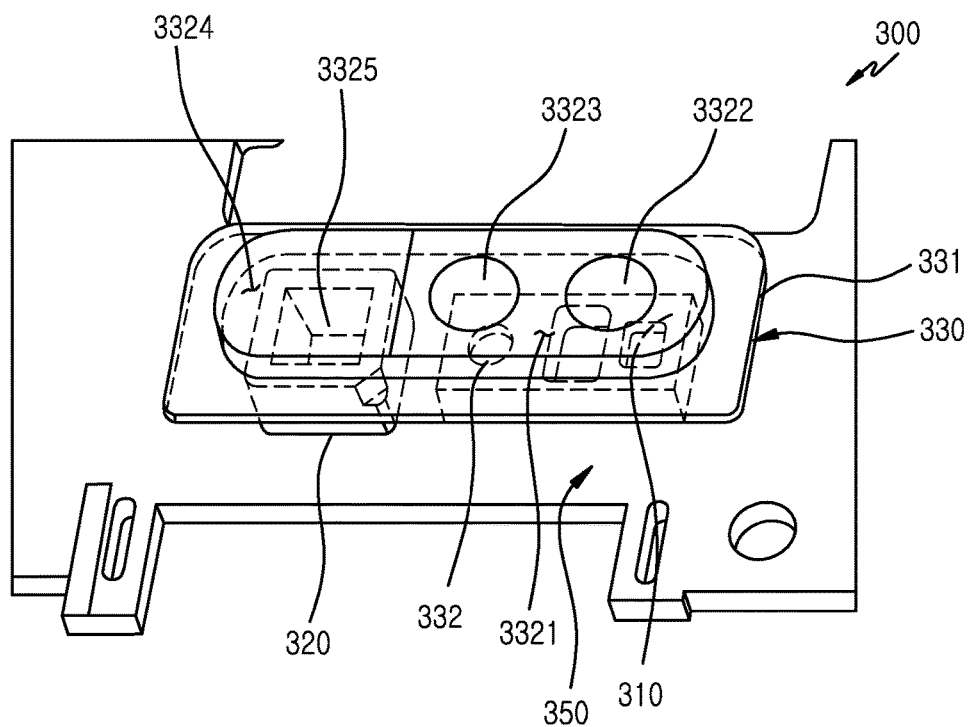
FIG. 5 illustrates a perspective view of an HR sensor device in an assembled state according to various embodiments of the present disclosure.
Figure 6:
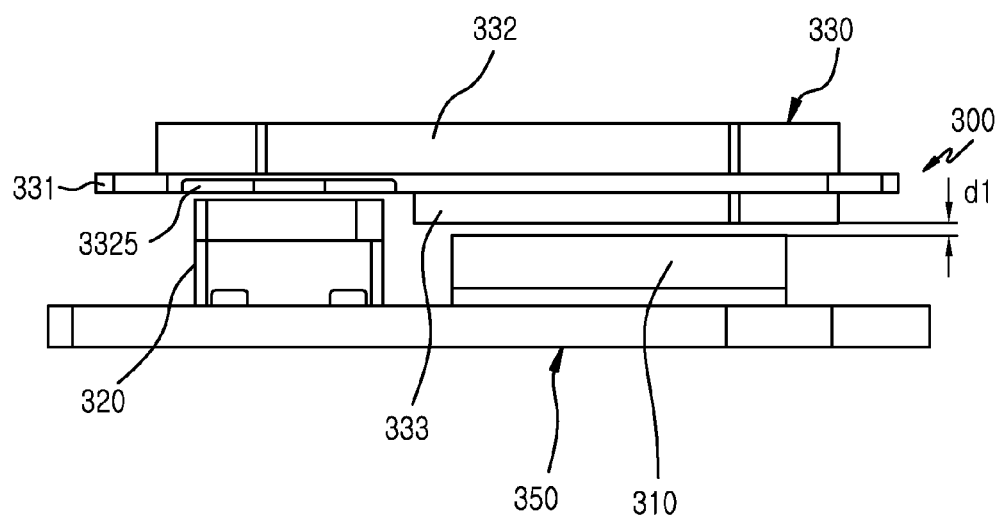
FIG. 6 illustrates a side view of an HR sensor device in an assembled state according to various embodiments of the present disclosure.

FIG. 5 illustrates a perspective view of an HR sensor device in an assembled state according to various embodiments of the present disclosure. FIG. 6 illustrates a side view of an HR sensor device in an assembled state according to various embodiments of the present disclosure.

Referring to FIGS. 5 and 6, the HR sensor device 300 may include a substrate 350, an HR sensor 310 and a flash LED 320 which are mounted on a top of the substrate 350, and a window 330 which is placed over the HR sensor 310 and the flash LED 320. According to an embodiment of the present disclosure, the window 330 may be placed such that a flash area 3324 formed on a first protrusion 332 vertically overlaps with the flash LED 320 and an HR sensor area 3321 formed on the first protrusion 332 vertically overlaps with the HR sensor 310. According to an embodiment of the present disclosure, a second protrusion 333 of the window 330 may be placed on an area which vertically overlaps with the HR sensor 310.

According to an embodiment of the present disclosure, the substrate 350 may include a rigid type substrate (e.g., a Printed Circuit Board (PCB)) where the HR sensor 310 and the flash LED 320 may be mounted. However, this should not be considered as limiting and the substrate 350 may include a flexible PCB (FPCB). According to an embodiment of the present disclosure, at least one of the HR sensor 310 and the flash LED 320 may not be mounted on the substrate 350 and may be placed on a structure placed in the electronic device. According to an embodiment of the present disclosure, at least one of the HR sensor 310 and the flash LED 320 may be mounted on the substrate 350 by Surface Mount Technology (SMT).

Referring to FIG. 6, the HR sensor 310 may be placed away from the second protrusion 333 of the window 330 by a specified distance d1. The distance d1 may be determined by considering the performance of the HR sensor 310 in the area of the second protrusion 333 except for the light emitting waveguide portion 3322 and the light receiving waveguide 3323. According to an embodiment of the present disclosure, the distance d1 may be less than or equal to 0.2 mm. However, this should not be considered as limiting and the HR sensor 310 and the second protrusion 333 may be placed in contact with each other.

Figure 7A:
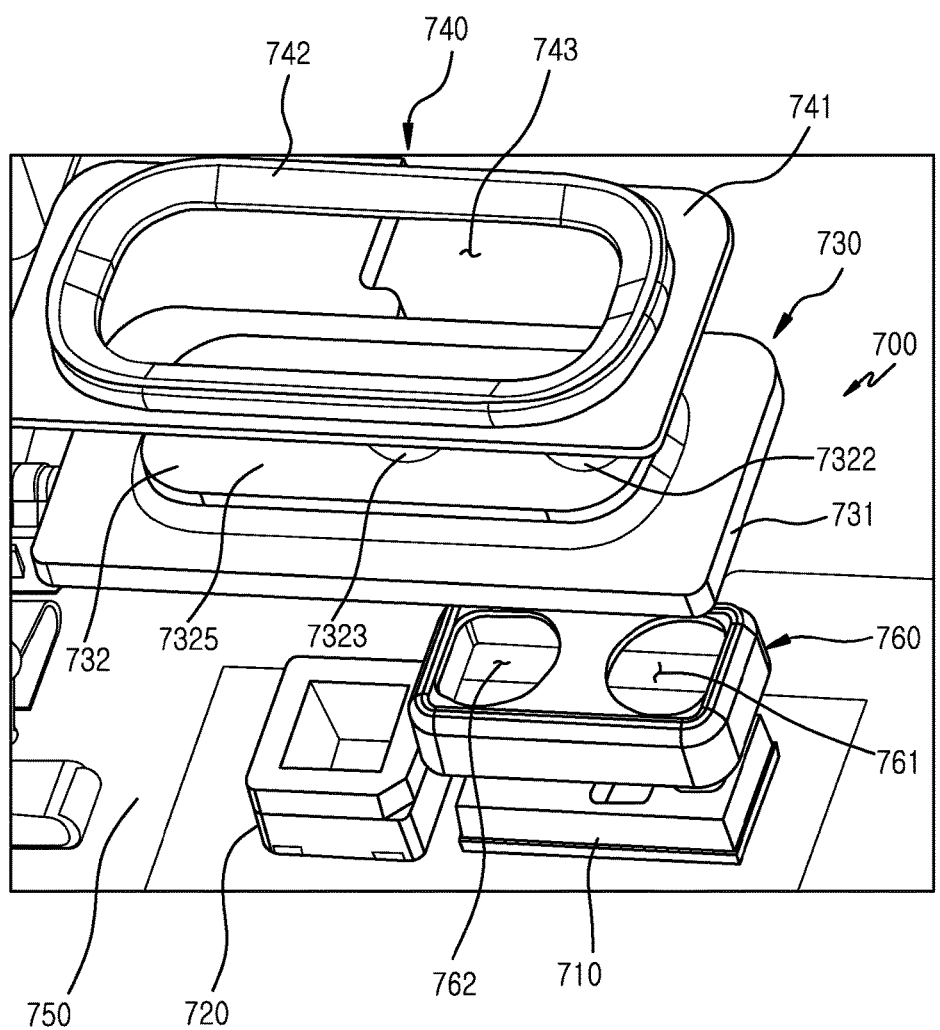
FIG. 7A illustrates an exploded perspective view of an HR sensor device according to various embodiments of the present disclosure.

FIG. 7A illustrates an exploded perspective view of an HR sensor device according to various embodiments of the present disclosure. According to an embodiment of the present disclosure, an HR sensor device 700 may be the HR sensor device 205 or 255 shown in FIGS. 2A, 2B, and 2C, for example.

Referring to FIG. 7A, the HR sensor device 700 may include an HR sensor 710 and a flash LED 720 which are arranged parallel with each other in the electronic device (e.g., the electronic device 200). According to an embodiment of the present disclosure, a window 730 at least a part of which is optically transparent may be placed over the HR sensor 710 and the flash LED 720, and a decoration member 740 may be placed over the window 730 to support the window 730.

According to an embodiment of the present disclosure, the window 730 may have a size to cover the HR sensor 710 and the flash LED 720 simultaneously. According to an embodiment of the present disclosure, the window 730 may include a plate 731 of a specified area and a protrusion 732 protruding from a top surface of the plate 731. The protrusion 732 may be coupled to the decoration member 740 by being seated on the decoration member 740 through an opening 743 of the decoration member 740, such that a flash waveguide portion 7325 of the protrusion 732 corresponding to the flash LED 720 and a light emitting waveguide portion 7322 and a light receiving waveguide 7323 of the protrusion 732 corresponding to the HR sensor 710 are exposed to an external surface of an external housing of the electronic device. According to an embodiment of the present disclosure, at least the flash waveguide portion 7325, the light emitting waveguide portion 7322, and the light receiving waveguide 7323 of the window 730 may be transparent.

According to various embodiments of the present disclosure, the decoration member 740 may include a flange 741 fixed to the external housing of the electronic device, and an exposure portion 742 protruding from the flange 741 and exposed to the outside of the external housing of the electronic device. According to an embodiment of the present disclosure, the decoration member 740 may have the opening 743 to accommodate the protrusion 732 of the window 730, and the exposure portion 742 may protrude along an edge of the opening 743.

According to various embodiments of the present disclosure, the window 730 may be formed to accommodate the HR sensor 710 and the flash LED 720, which perform different operations, all together. According to an embodiment of the present disclosure, the HR sensor 710 may further include a shielding member 760 to prevent interference by the flash LED 720 which performs a different operation from that of the HR sensor 710. According to an embodiment of the present disclosure, the shielding member 760 may be formed in a cover type to cover the entirety of the HR sensor 710 except for openings 761 and 762 corresponding to a light emitting area and a light receiving area of the HR sensor 710. According to an embodiment of the present disclosure, the shielding member 760 may be formed from an opaque material. According to an embodiment of the present disclosure, the shielding member 760 may be formed from various materials, such as rubber, urethane, PC, and the like.

Figure 7B:
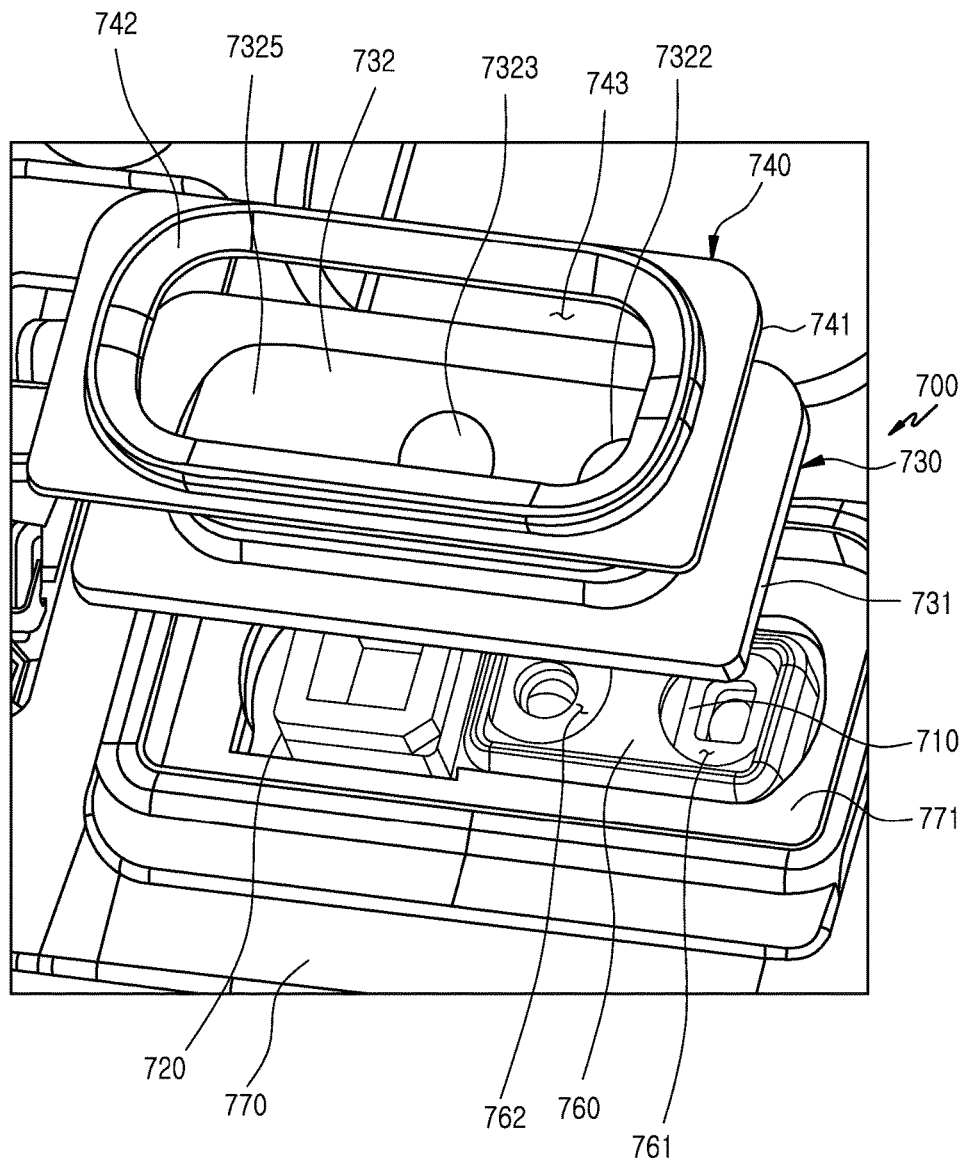
FIG. 7B illustrates an exploded perspective view of an HR sensor device according to various embodiments of the present disclosure.

FIG. 7B illustrates an exploded perspective view of an HR sensor device according to various embodiments of the present disclosure.

Referring to FIG. 7B, the HR sensor device 700 has the same configuration as that of the HR sensor device of FIG. 7A, and FIG. 7B illustrates the window 730 and the decoration member 740 being placed in an external housing 770 of the electronic device. According to an embodiment of the present disclosure, the external housing 770 may include a plate seating portion 771 including an opening through which the HR sensor 710 and the flash LED 720 are exposed. According to an embodiment of the present disclosure, the plate 731 of the window 730 may be fixed by being seated on the plate seating portion 771 of the external housing 770. According to an embodiment of the present disclosure, the plate 731 may be fixed to the plate seating portion 771 of the external housing 770 by a double-sided tape, bonding, ultrasound fusion, and the like.

According to an embodiment of the present disclosure, the decoration member 740 may be fixed to the top of the window 730 fixed to the plate seating portion 771 of the external housing 770 by a double-sided tape, bonding, ultrasound fusion, and the like. According to an embodiment of the present disclosure, the decoration member 740 may be fixed by letting the protrusion 732 of the window 730 pass through the opening 743, and may be fixed by bringing its bottom surface into contact with the top surface of the plate 731 of the window 730 along the edge of the decoration member 740.

Figure 8:
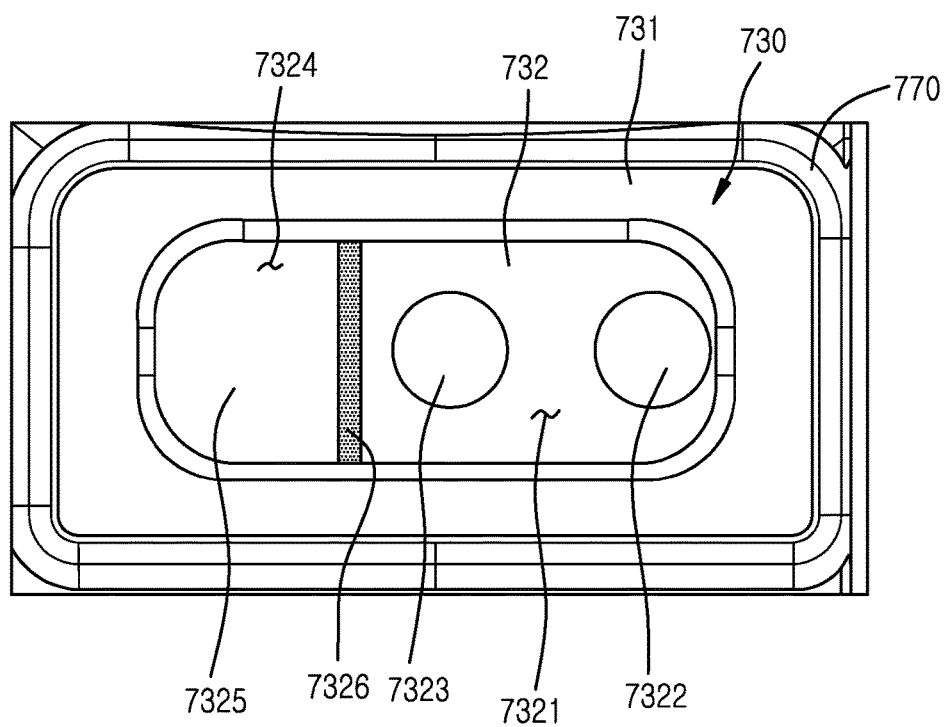
FIG. 8 illustrates a plane view of a window of an HR sensor device according to various embodiments of the present disclosure.

FIG. 8 illustrates a plane view of a window of an HR sensor device according to various embodiments of the present disclosure.

Referring to FIG. 8, a flash area 7324 and an HR sensor area 7321 of a top surface of a window 730 may be optically separated from each other by a shielding boundary portion 7326 formed on the top surface of the window 730. According to an embodiment of the present disclosure, the shielding boundary portion 7326 may be formed by corroding the top surface of the window 730. According to an embodiment of the present disclosure, the window 730 which is placed on an external housing 770 may apply a single body, but may maintain a flash waveguide portion 7325 of the flash area 7324 and a light emitting waveguide portion 7322 and a light receiving waveguide portion 7323 of the HR sensor area 7321 being optically separated from each other by the shielding boundary portion 7326.

Figure 9:
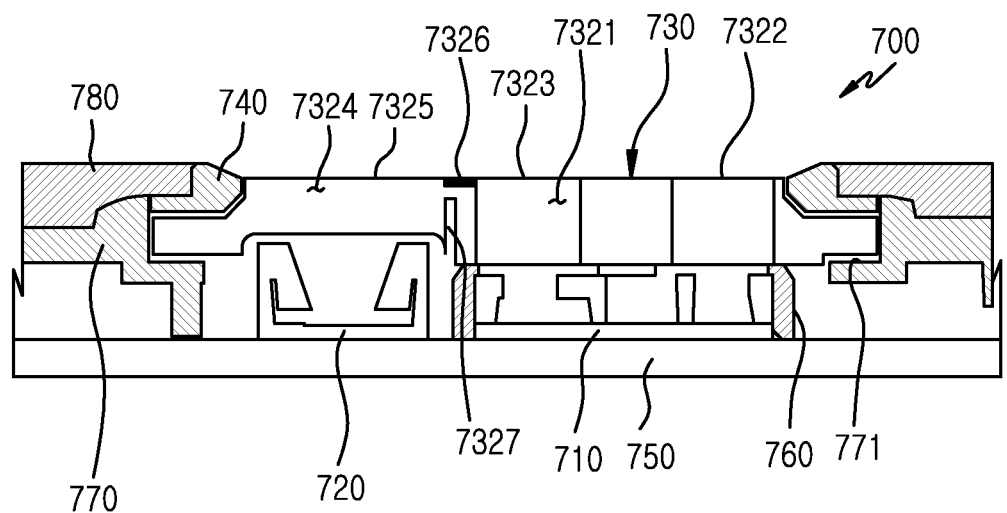
FIG. 9 illustrates a cross section view of main parts of an HR sensor device according to various embodiments of the present disclosure.

FIG. 9 illustrates a cross section view of main parts of an HR sensor device according to various embodiments of the present disclosure.

Referring to FIG. 9, the HR sensor device 700 may include a substrate 750, an HR sensor 710 which is mounted on a top of the substrate 750, a flash LED 720 which is mounted on the substrate parallel with the HR sensor 710, and a window 730 for covering the HR sensor 710 and the flash LED 720. According to an embodiment of the present disclosure, the window 730 may be fixed by being seated on a plate seating portion 771 formed on an external housing 770. According to an embodiment of the present disclosure, the window 730 may be placed such that a flash area 7324 vertically overlaps with the flash LED 720 and an HR sensor area 7321 vertically overlaps with the HR sensor 710.

According to an embodiment of the present disclosure, the substrate 750 may include a rigid type substrate (e.g., a PCB) where the HR sensor 710 and the flash LED 720 may be mounted. However, this should not be considered as limiting and the substrate 750 may include an FPCB. According to an embodiment of the present disclosure, at least one of the HR sensor 710 and the flash LED 720 may not be mounted on the substrate 750 and may be placed in a structure placed in the electronic device. According to an embodiment of the present disclosure, at least one of the HR sensor 710 and the flash LED 720 may be mounted on the substrate 750 by SMT.

According to an embodiment of the present disclosure, a decoration member 740 may be placed on a top of the window 730. The decoration member 740 may be placed to further protrude than the external housing 770 forming an external surface of the electronic device. According to an embodiment of the present disclosure, the external housing 770 may further include a battery cover 780 formed on a top thereof. The decoration member 740 may be formed to coincide with a surface of the battery cover 780 placed on the external housing 770. However, this should not be considered as limiting and the decoration member 740 may be formed to be higher or lower than the surface of the external housing 770 or the battery cover 780.

According to an embodiment of the present disclosure, the window 730 may be placed to be lower than the decoration member 740. According to an embodiment of the present disclosure, the window 730 may be formed to be lower than the external housing or the battery cover 780 in a configuration without the decoration member 740, or may be formed to be lower than the decoration member 740 but higher than the external housing or the battery cover 780 in a configuration with the decoration member 740.

According to an embodiment of the present disclosure, the window 730 may include a shielding boundary portion 7326 having a top portion corroded to optically separate the flash area 7324 and the HR sensor area 7321 from each other. According to an embodiment of the present disclosure, the window 730 may further include a shielding recess 7327 formed to make a cut from a bottom surface of the window 730 to a part of the upper side. According to an embodiment of the present disclosure, the flash area 7324 and the HR sensor area 7321 may be optically separated from each other by the shielding recess 7327. According to an embodiment of the present disclosure, the shielding recess 7327 may serve to optically shield by itself, and additionally or alternatively, may be filled with an opaque material.

According to various embodiments of the present disclosure, for the purpose of shielding a flash waveguide portion 7325 of the flash area 7324 and a light emitting waveguide portion 7322 and a light receiving waveguide portion 7323 of the HR sensor area 7321, a shielding member 760 for covering the HR sensor 710, the shielding boundary portion 7326 formed on the top surface of the window 730, and the shielding recess 7327 formed on the bottom surface of the window 730 may be applied. At least one of the shielding units may be applied.

Figure 10:
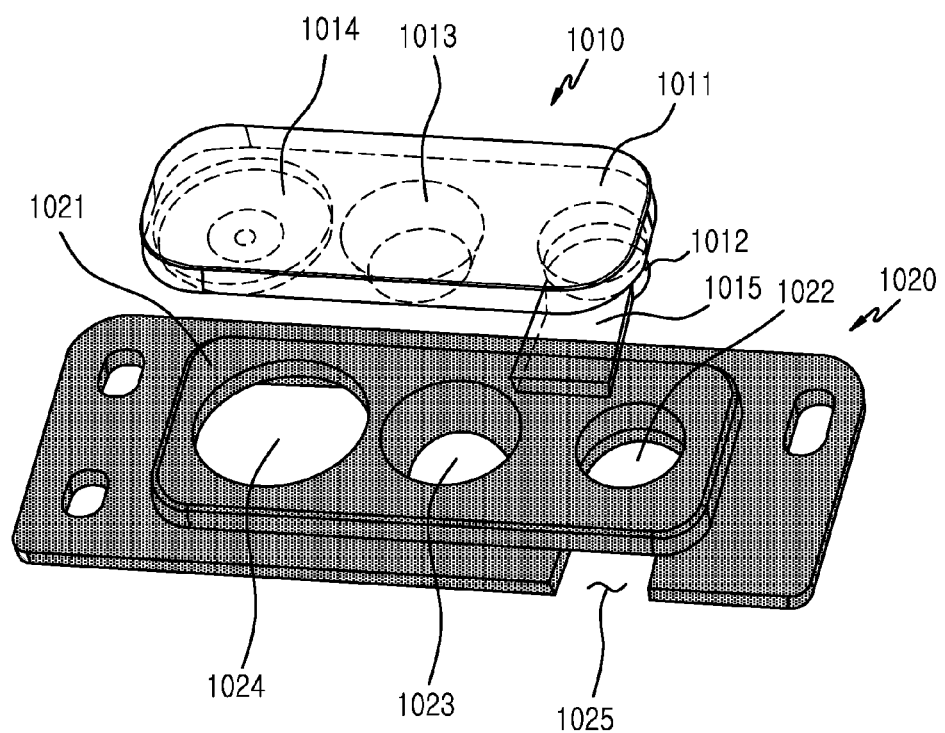
FIG. 10 illustrates an exploded perspective view of a transparent window and a shielding member applied to an HR sensor device according to various embodiments of the present disclosure.

FIG. 10 illustrates an exploded perspective view of a transparent window and a shielding member which are included in an HR sensor device according to various embodiments of the present disclosure. A transparent window 1010 according to an embodiment of the present disclosure may be the window 730 shown in FIG. 7. A shielding member 1020 according to an embodiment of the present disclosure may be the shielding member 760 shown in FIG. 7.

Referring to FIG. 10, the transparent window 1010 and the shielding member 1020 may be formed as a single window member by dual injection molding. According to an embodiment of the present disclosure, the shielding member 1020 may be formed by first injection molding and then the transparent window 1010 may be formed by second injection molding.

According to an embodiment of the present disclosure, the operation of forming the integral window includes the operations of forming a cavity corresponding to a shape of the transparent window 1010 and the shielding member 1020 by combining a first mold and a second mold which are separated from each other, charging the cavity by injecting a first melting resin through a first gate formed at one side of the cavity, cooling or hardening the first melting resin, charging the cavity by injecting a second melting resin through a second gate formed at one side of the cavity, cooling or hardening the second melting resin, extracting a molding product by removing the first mold and the second mold, and cutting the gates and unnecessary parts (e.g., a gate runner, a reinforcing rib, and the like) from the molding product.

According to an embodiment of the present disclosure, the shielding member 1020 may include a first opening 1022, a second opening 1023, and a third opening 1024 formed on a plate type window mounting portion 1021 parallel with one another. Referring to the above-described drawings, the first opening 1022 may be formed on a location corresponding to the light emitting waveguide portion of the HR sensor, the second opening 1023 may be formed on a location corresponding to the light receiving waveguide portion of the HR sensor, and the third opening 1024 may be formed on a location corresponding to the flash waveguide portion.

According to an embodiment of the present disclosure, the shielding member 1020 may further include a gate receiver 1025 which is a molding material injection path to form the transparent window 1010 by the second injection molding. The gate receiver 1025 may be formed to be connected with the first opening 1022. However, this should not be considered as limiting and the gate receiver 1025 may be formed on an area corresponding to at least one of an upper side, a lower side, a left side, and a right side of the transparent window 1010 according to a shape and a characteristic of the transparent window 1010.

According to an embodiment of the present disclosure, after the shielding member 1020 is formed by the first injection molding, the second injection molding is performed to inject a molding material through the gate receiver 1025 to form the transparent window 1010. By the second injection molding, the transparent window 1010 may be formed starting with an injection gate 1015. Specifically, a plate 1011 may be formed on a location corresponding to a window mounting portion 1021 of the shielding member 1020, and a first protrusion 1012 to be inserted into the first opening 1022 of the shielding member 1020, a second protrusion 1013 to be injected into the second opening 1023, and a third protrusion 1014 to be injected into the third opening 1024 may be formed on the plate 1011. According to an embodiment of the present disclosure, the first opening 1022 and the second opening 1023 may have an external surface inclined to correspond to an incidence angle/emission angle of infrared rays of the HR sensor.

Figure 11A:
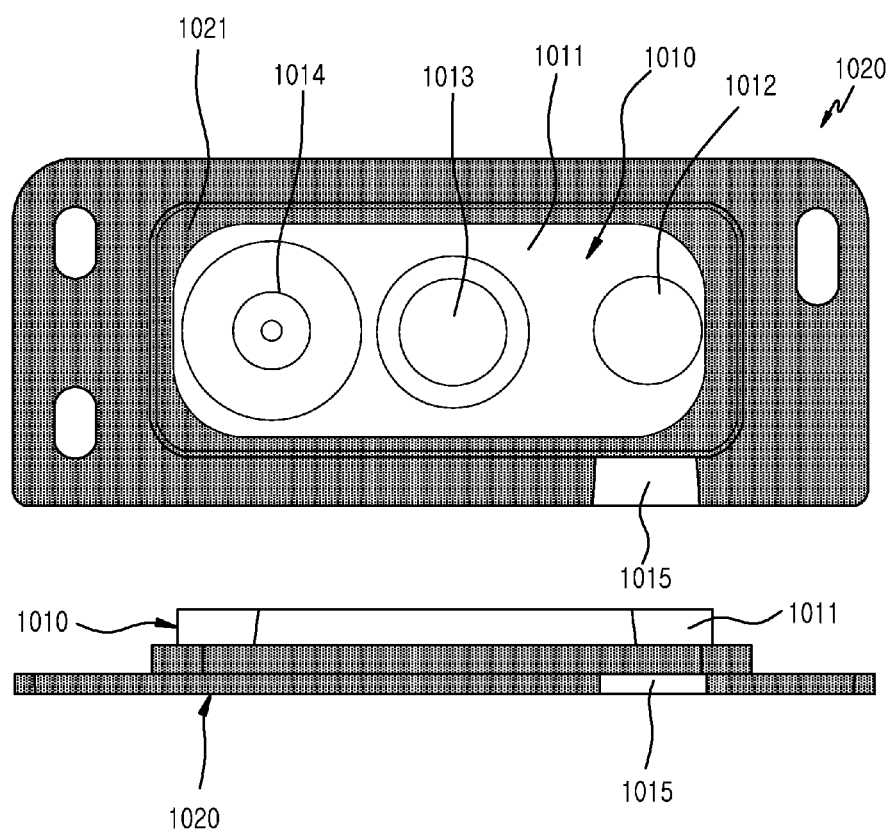
FIG. 11A illustrates a plane view and a side view of a transparent window and a shielding member which are coupled to each other to be applied to an HR sensor device according to various embodiments of the present disclosure.
Figure 11B:
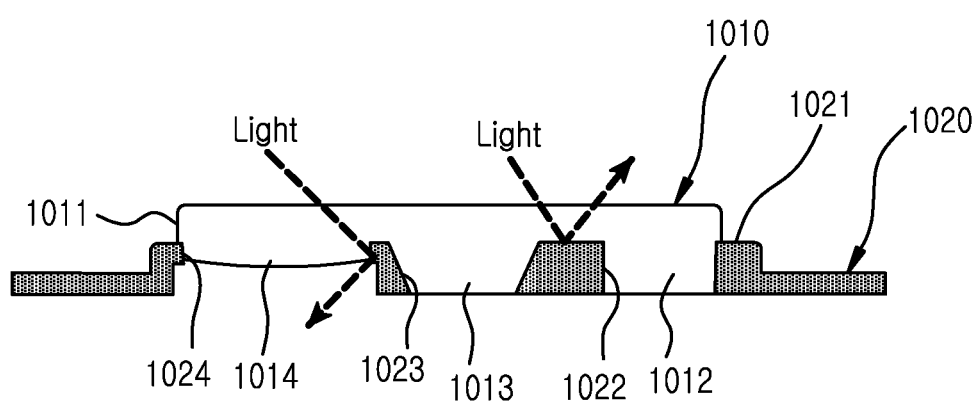
FIG. 11B illustrates a light reflection operation performed by a shielding member coupled to a transparent window according to various embodiments of the present disclosure.
Figure 11C:
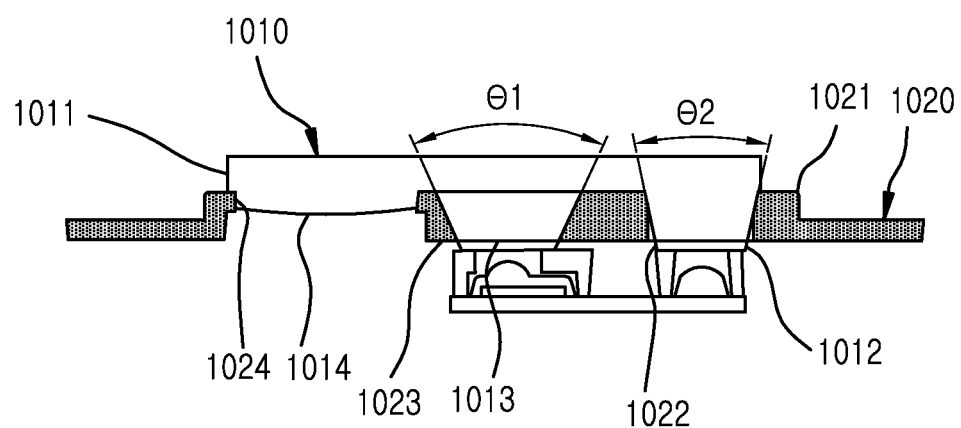
FIG. 11C illustrates light incidence and emission angles regulated by a shielding member coupled to a transparent window according to various embodiments of the present disclosure.

FIG. 11A illustrates a plane view and a side view of a transparent window and a shielding member which are coupled to each other to be applied to an HR sensor device in an assembled state according to various embodiments of the present disclosure. FIG. 11B illustrates a light reflection operation performed by a shielding member coupled to a transparent window according to various embodiments of the present disclosure. FIG. 11C illustrates light incidence and emission angles regulated by a shielding member coupled to a transparent window according to various embodiments of the present disclosure.

Referring to FIG. 11A, a plate 1011 of a specified height may be formed on a top surface of a window mounting portion 1021 of the shielding member 1020 by double injection molding, and the shielding member 1020 is interposed between a first protrusion 1012, a second protrusion 1013, and a third protrusion 1014 of the transparent window 1010 such that the optical role of each of the protrusions 1012, 1013, and 1014 are not interfered by one another.

Referring to FIG. 11B, the shielding member 1020 is interposed between the first protrusion 1012 and the second protrusion 1013, thereby preventing unnecessary external light from entering. According to an embodiment of the present disclosure, the shielding member 1020 is also interposed between the second protrusion 1013 and the third protrusion 1014, thereby preventing unnecessary external light from entering.

Referring to FIG. 11C, the first protrusion 1012 and the second protrusion 1013 may be formed to have specified angles θ1 and θ2. According to an embodiment of the present disclosure, a first opening 1022 and a second opening 1023 of the shielding member 1020 may be tapered to have a width gradually narrower from the top to the bottom. Accordingly, the first protrusion 1012 and the second protrusion 1013 of the transparent window 1010 filled in the openings 1022 and 1023, respectively, may be formed to have corresponding angles.

Figure 12:
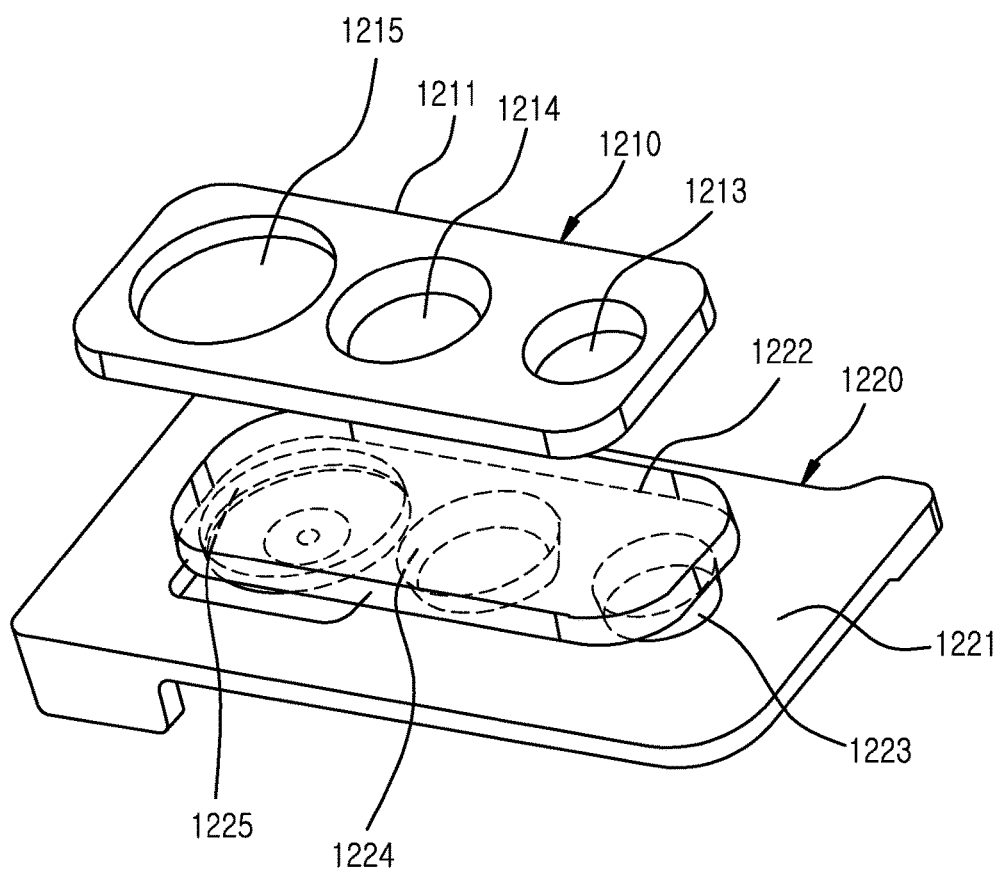
FIG. 12 illustrates an exploded perspective view of a transparent window and a shielding member applied to an HR sensor device according to various embodiments of the present disclosure.
Figure 13:
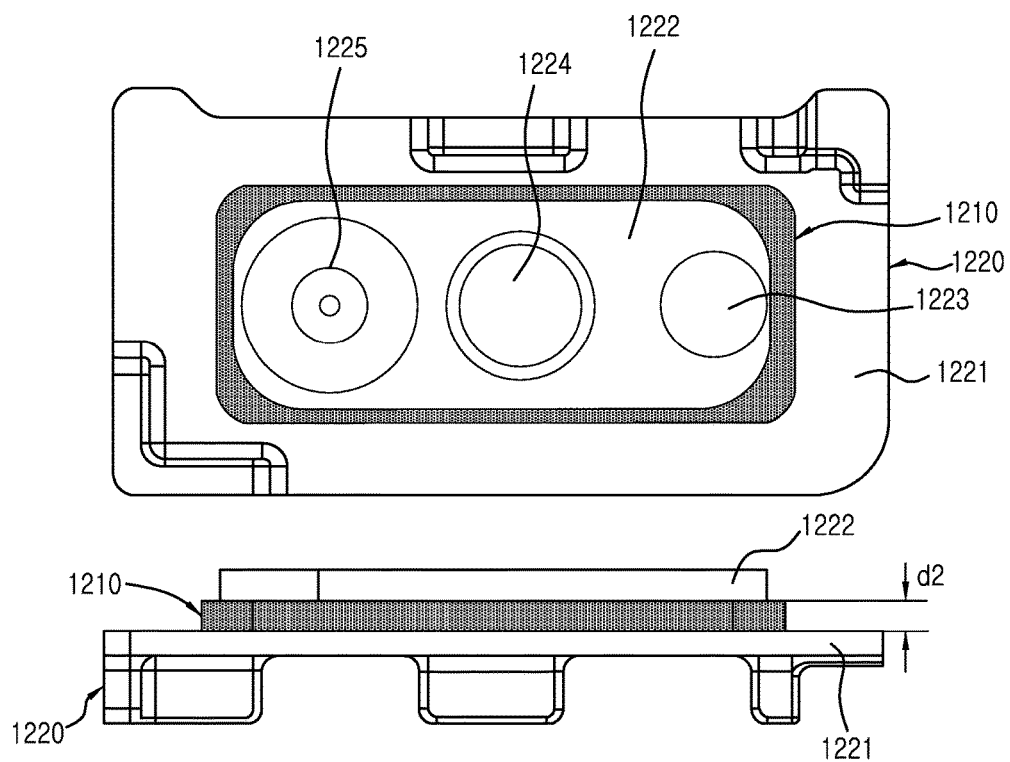
FIG. 13 illustrates a plane view and a side view of a transparent window and a shielding member which are coupled to each other to be applied to an HR sensor device according to various embodiments of the present disclosure.

FIG. 12 illustrates an exploded perspective view of a transparent window and a shielding member which are applied to an HR sensor device according to various embodiments of the present disclosure. FIG. 13 illustrates a plane view and a side view of a transparent window and a shielding member which are coupled to each other to be applied to an HR sensor device in an assembled state according to various embodiments of the present disclosure.

Referring to FIGS. 12 and 13, a shielding member 1210 is insert-molded into a transparent window 1220 such that a single window member is formed.

According to an embodiment of the present disclosure, the shielding member 1210 may include a first penetrating hole 1213, a second penetrating hole 1214, and a third penetrating hole 1215 formed on a plate 1211 parallel with one another. According to an embodiment of the present disclosure, referring to the above-described drawings, the first penetrating hole 1213 may be formed on a location corresponding to the light emitting waveguide portion of the HR sensor. The second penetrating hole 1214 may be formed on a location corresponding to the light receiving waveguide portion of the HR sensor, for example. The third penetrating hole 1215 may be formed on a location corresponding to the flash waveguide portion, for example.

According to an embodiment of the present disclosure, the transparent window 1220 may include a first plate 1221 and a second plate 1222 which is formed above a top of the first plate 1221 higher than the first plate 1221 by a specified height d2. According to an embodiment of the present disclosure, the first plate 1221 and the second plate 1222 may be connected with each other by a first connecting portion 1223, a second connecting portion 1224, and a third connecting portion 1225. According to an embodiment of the present disclosure, the first connecting portion 1223, the second connecting portion 1224, and the third connecting portion 1225 may be formed on locations corresponding to the first penetrating hole 1213, the second penetrating hole 1214, and the third penetrating hole 1215, respectively.

According to an embodiment of the present disclosure, the first, second, and third connecting portions 1223, 1224, and 1225 may be molded by penetrating through the first penetrating hole 1213, the second penetrating hole 1214, and the third penetrating hole 1215 of the shielding member, respectively.

According to an embodiment of the present disclosure, the insert-molded shielding member 1210 is interposed between the first connecting portion 1223 and the second connecting portion 1224, thereby optically blocking the first connecting portion 1223 and the second connecting portion 1224 from each other and thus preventing interference therebetween. According to an embodiment of the present disclosure, the insert-molded shielding member 1210 is interposed between the second connecting portion 1224 and the third connecting portion 1225, thereby optically blocking the second connecting portion 1224 and the third connecting portion 1225 from each other and thus preventing interference therebetween.

According to an embodiment of the present disclosure, the operation of molding the shielding member 1210 includes the operation of forming a cavity corresponding to a shape of the shielding member 1210 by combining a first mold and a second mold which are separated from each other, charging the cavity by injecting a melting resin through a gate provided at one side of the cavity, cooling or hardening the melting resin, extracting a molding product by removing the first mold and the second mold, and cutting the gate and unnecessary parts (e.g., a gate runner, a reinforcing rib, and the like) from the molding product.

An integral window may be manufactured by using the shielding member 1210 manufactured in the above-described operations. The operation of molding the integral window includes the operations of forming a cavity corresponding to a shape of the integral window by combining a first mold and a second mold which are separated from each other, placing the shielding member 1210 at one side of the cavity, charging the cavity by injecting a melting resin through a gate provided at one side of the cavity, cooling or hardening the melting resin, extracting a molding product by removing the first mold and the second mold, and cutting the gate and unnecessary parts (e.g., a gate runner, a reinforcing rib, and the like) from the molding product.

However, this should not be considered as limiting. The transparent window 1220 may be manufactured by injection molding first and then the shielding member 1210 may be injection molded by placing the transparent window 1220 in an insert mold.

According to various embodiments of the present disclosure, a mobile electronic device may be provided. According to an embodiment of the present disclosure, the mobile electronic device may include at least one processor, a display module electrically connected with the processor and including a touch screen, a communication module electrically connected with the processor, a portable electronic device housing configured to house at least a part of the display module, the at least one processor, and the communication module, and an HR sensor (e.g., an HRM sensor) which is placed on one surface of the housing and has at least its part exposed to an outside, and which is electrically connected with the processor.

According to various embodiments of the present disclosure, the HR sensor may be included in a second surface of the housing opposite to a first surface of the housing which includes the touch screen.

According to various embodiments of the present disclosure, the second surface of the housing may include a first side, a second side which is longer than the first side and is perpendicular to the first side, a third side which has a same length as that of the first side and is parallel to the first side, and a fourth side which has a same length as that of the second side and is parallel to the second side, and the HR sensor may be located between an imaginary line which crosses over a ⅓ point of the length of the second side from the first side, and the first side.

According to various embodiments of the present disclosure, the mobile electronic device may further include a camera which is exposed to an outside through a part of the housing, and the HR sensor may be placed adjacent to the camera.

According to various embodiments of the present disclosure, the HR sensor may include a window at least a part of which is transparent, and a top surface of the window may not protrude further than a surface of a portion of the housing, the portion surrounding the HR sensor, or may be located in a dent formed from a surface of the housing.

According to various embodiments of the present disclosure, the HR sensor may include a window at least a part of which is transparent, and a top surface of the window may not protrude further than a surface of a portion of a decoration member, the portion surrounding the HR sensor, or may be located in a dent formed from a surface of the decoration member.

According to various embodiments of the present disclosure, the electronic device may include at least one electronic component which is exposed through a part of the housing, and the HR sensor may be placed adjacent to the electronic component.

According to various embodiments of the present disclosure, the electronic component may include an LED.

According to various embodiments of the present disclosure, the mobile electronic device may further include an integral window configured to cover the HR sensor and the at least one electronic component all together.

According to various embodiments of the present disclosure, the integral window may include a first member (e.g., the transparent window 1220) which comprises a top portion (e.g., the second plate 1222), a bottom portion (e.g., the first plate 1221), and a connecting portion (e.g., the first, second, and third connecting portions 1223, 1224, and 1225) for connecting the top portion 1222 and the bottom portion 1221, and may include a transparent material. The integral window may include a second member (e.g., the shielding member 1210) which is in contact with the top portion and the bottom portion, is interposed between the top portion and the bottom portion, includes at least one penetrating hole (e.g., the first penetrating hole 1213, the second penetrating hole 1214, or the third penetrating hole 1215), and includes at least one of a translucent material and an opaque material. The top portion, the bottom portion, and the connecting portion may be integrally formed with one another. In addition, the connecting portion of the first member penetrates through the penetrating hole and is almost wholly in contact with an inner wall of the penetrating hole. According to various embodiments of the present disclosure, the integral window may be formed by forming the shielding member of the opaque material first and then forming the HR sensor area and the area of the electronic component with the transparent material second.

According to various embodiments of the present disclosure, the integral window may be formed by forming other portions except for the HR sensor area and the area of the electronic component of a window member of a transparent material by using a shielding member of an opaque material.

According to various embodiments of the present disclosure, the integral window may print a rear surface except for the HR sensor area and the area of the electronic component with an opaque material, and shields the HR sensor and the electronic component.

According to various embodiments of the present disclosure, the electronic component is a flash LED.

According to various embodiments of the present disclosure, an electronic device may be provided. The electronic device may include a substrate, an HR sensor which is mounted on the substrate, a flash LED which is placed adjacent to the HR sensor, an integral window which is placed in a housing to cover the HR sensor and the flash LED all together, and a shielding unit configured to provide shielding between an area of the HR sensor and an area of the flash LED.

According to various embodiments of the present disclosure, a surface of the integral window may coincide with a surface of the housing or may be lower than the surface of the housing.

According to various embodiments of the present disclosure, the integral window may be formed by double injection molding, the double injection molding forming a shielding member of an opaque material by first injection molding and then forming the area of the HR sensor and the area of the electronic component with a transparent material by second injection molding.

According to various embodiments of the present disclosure, the integral window may be formed by insert-molding other portions except for the area of the HR sensor and the area of the electronic component of a window member of a transparent material by using a shielding member of an opaque material.

According to various embodiments of the present disclosure, the integral window may be treated to shield by printing a rear surface except for the area of the HR sensor area and the area of the electronic component with an opaque material.

According to various embodiments of the present disclosure, a method for using an electronic device may be provided. The method may include gripping, by a user, a mobile electronic device comprising a display with one hand of the user, bringing one of user's fingers into contact with an HR sensor comprised in one surface of a housing of the mobile electronic device, and acquiring information based on data acquired by the sensor through the display of the mobile electronic device.

According to various embodiments of the present disclosure, a method for operating an electronic device may be provided. The method may include receiving, by a mobile device comprising a housing accommodating at least a part of a display, a processor, a communication module, and an HR sensor, a user input requesting driving of an application program, detecting, by the HR sensor, a change from a part of a user's body and acquiring data, and, based on at least a part of the acquired data, displaying, by the processor, information on the display through a user interface of the application program.

According to various embodiments of the present disclosure, the method may further include transmitting at least a part of the data through a communication module.

Figure 14:
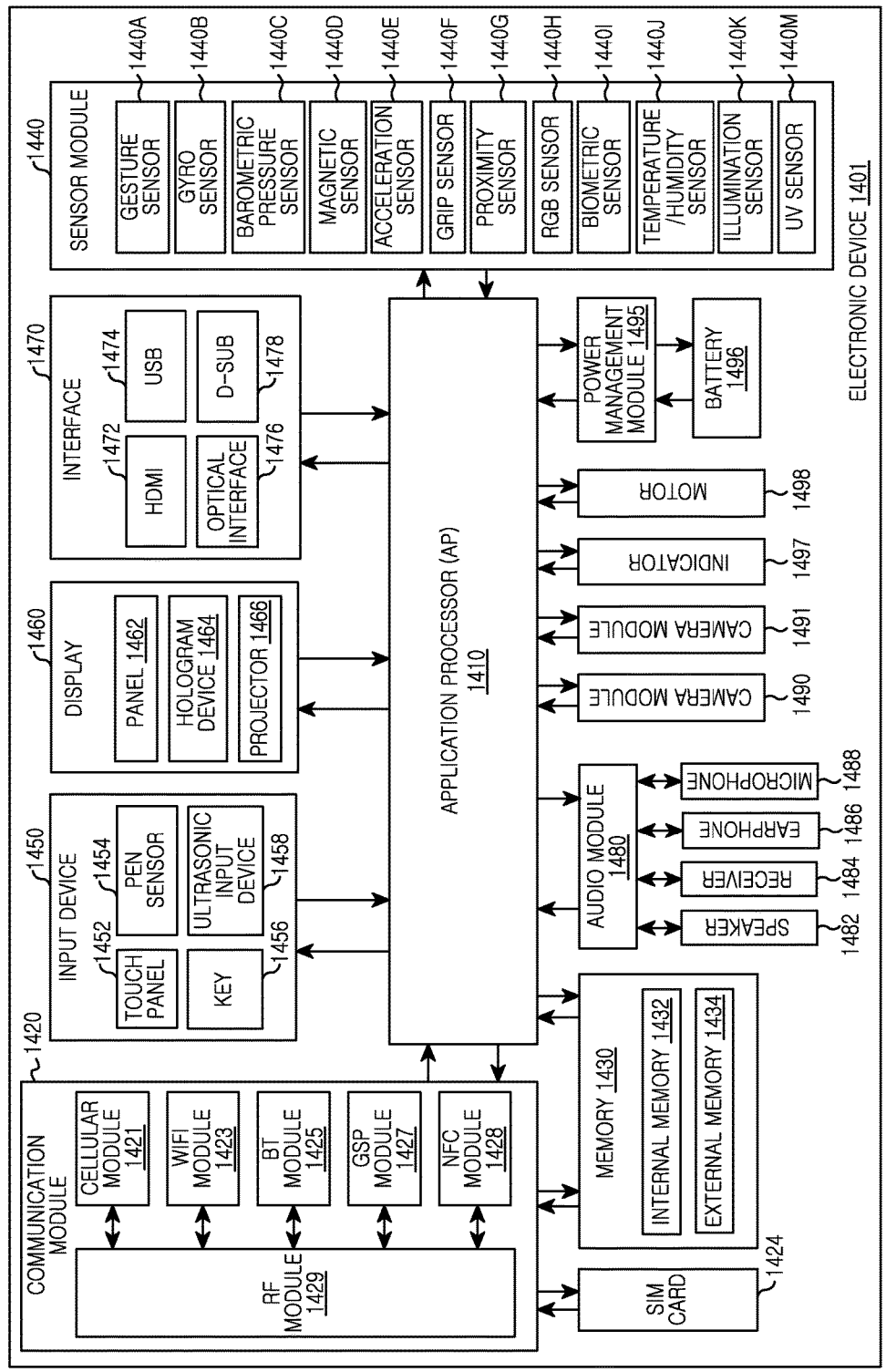
FIG. 14 illustrates a block diagram of an electronic device according to various embodiments of the present disclosure.

FIG. 14 illustrates a block diagram of an electronic device according to various embodiments of the present disclosure.

Referring to FIG. 14, an electronic device 1401 may configure an entirety or part of the electronic device 101 shown in FIG. 1.

Referring to FIG. 14, the electronic device 1401 may include one or more Application Processors (APs) 1410, a communication module 1420, a Subscriber Identification Module (SIM) card 1424, a memory 1430, a sensor module 1440, an input device 1450, a display 1460, an interface 1470, an audio module 1480, camera modules 1490 and 1491, a power management module 1495, a battery 1496, an indicator 1497, or a motor 1498.

The AP 1410 may control a plurality of hardware or software elements connected to the AP 1410 by driving an operating system or an application program, and may process and calculate a variety of data including multimedia data. For example, the AP 1410 may be implemented by using a System on Chip (SoC). According to an embodiment of the present disclosure, the AP 1410 may further include a Graphics Processing Unit (GPU) (not shown).

The communication module 1420 (e.g., the communication interface 160) may transmit and receive data in communication between the electronic device 1401 (e.g., the electronic device 101) and other electronic devices (e.g., the electronic device 104 or the sever 106) connected through a network. According to an embodiment of the present disclosure, the communication module 1420 may include a cellular module 1421, a WiFi module 1423, a BT module 1425, a GPS module 1427, an NFC module 1428, and a Radio Frequency (RF) module 1429.

The cellular module 1421 may provide a voice call, a video call, a text service, or an Internet service through a telecommunications network (e.g., LTE, LTE-A, CDMA, WCDMA, UMTS, WiBro, GSM, and the like). In addition, the cellular module 1421 may identify and authenticate the electronic device in the telecommunications network by using a subscriber identification module (e.g., the SIM card 1424). According to an embodiment of the present disclosure, the cellular module 1421 may perform at least some of the functions provided by the AP 1410. For example, the cellular module 1421 may perform at least some of the multimedia control functions.

According to an embodiment of the present disclosure, the cellular module 1421 may include a Communication Processor (CP). In addition, the cellular module 1421 may be implemented by using an SoC, for example. Referring to FIG. 14, the cellular module 1421 (e.g., the communication processor), the memory 1430, or the power management module 1495 are elements separate from the AP 1410. However, according to an embodiment of the present disclosure, the AP 1410 may be configured to include at least some of the above-described elements (e.g., the cellular module 1421).

According to an embodiment of the present disclosure, the AP 1410 or the cellular module 1421 (e.g., the communication processor) may load instructions or data received from a non-volatile memory connected therewith or at least one of the other elements into a volatile memory, and may process the instructions or data. In addition, the AP 1410 or the cellular module 1421 may store data which is received from at least one of the other elements or generated by at least one of the other elements in the non-volatile memory.

The WiFi module 1423, the BT module 1425, the GPS module 1427, or the NFC module 1428 each may include a processor for processing data received and transmitted through a corresponding module. Referring to FIG. 14, the cellular module 1421, the WiFi module 1423, the BT module 1425, the GPS module 1427, or the NFC module 1428 is illustrated in a separate block. However, according to an embodiment of the present disclosure, at least some (e.g., two or more) of the cellular module 1421, the WiFi module 1423, the BT module 1425, the GPS module 1427, or the NFC module 1428 may be included in a single integrated chip (IC) or a single IC package. For example, at least some of the processors corresponding to the cellular module 1421, the WiFi module 1423, the BT module 1425, the GPS module 1427, and the NFC module 1428 (e.g., the communication processor corresponding to the cellular module 1421 and the WiFi processor corresponding to the WiFi module 1423) may be implemented by using a single SoC.

The RF module 1429 may transmit and receive data, for example, may transmit and receive an RF signal. Although not shown, the RF module 1429 may include a transceiver, a Power Amp Module (PAM), a frequency filter, or a Low Noise Amplifier (LNA), for example. In addition, the RF module 1429 may further include a component for exchanging electromagnetic waves in a free space in wireless communication, for example, a conductor or conducting wire. Referring to FIG. 14, the cellular module 1421, the WiFi module 1423, the BT module 1425, the GPS module 1427, and the NFC module 1428 share the single RF module 1429 with one another. However, according to an embodiment of the present disclosure, at least one of the cellular module 1421, the WiFi module 1423, the BT module 1425, the GPS module 1427, or the NFC module 1428 may transmit and receive an RF signal through a single separate RF module.

The SIM card 1424 may be a card including a subscriber identification module, and may be inserted into a slot formed on a specific location of the electronic device. The SIM card 1424 may include its unique identification information (for example, an Integrated Circuit Card Identifier (ICCID)) or subscriber information (for example, International Mobile Subscriber Identity (IMSI)).

The memory 1430 (e.g., the memory 130) may include an internal memory 1432 or an external memory 1434. For example, the internal memory 1432 may include at least one of a volatile memory (for example, a Dynamic Random Access Memory (DRAM), a Static Random Access Memory (SRAM), a Synchronous DRAM (SDRAM), and the like) and a non-volatile memory (for example, a One-Time Programmable Read Only Memory (OTPROM), a Programmable Read Only Memory (PROM), an Erasable Programmable Read Only Memory (EPROM), an Electrically Erasable Programmable Read Only Memory (EEPROM), a mask ROM, a flash ROM, a Not And (NAND) flash memory, a Not Or (NOR) flash memory, and the like).

According to an embodiment of the present disclosure, the internal memory 1432 may be a Solid State Drive (SSD). The external memory 1434 may further include a flash drive, for example, Compact Flash (CF), Secure Digital (SD), Micro-SD, Mini-SD, extreme-Digital (xD), memory stick, and the like. The external memory 1434 may be functionally connected with the electronic device 1401 through various interfaces. According to an embodiment of the present disclosure, the electronic device 1401 may further include a storage device (or a storage medium), such as a hard drive.

The sensor module 1440 may measure a physical quantity or detect an operation state of the electronic device 1401, and may convert measured or detected information into electric signals. The sensor module 1440 may include at least one of a gesture sensor 1440A, a gyro sensor 1440B, a barometric pressure sensor 1440C, a magnetic sensor 1440D, an acceleration sensor 1440E, a grip sensor 1440F, a proximity sensor 1440G, a color sensor 1440H (e.g., Red, Green, Blue (RGB) sensor), a biosensor 1440I, a temperature/humidity sensor 1440J, an illumination sensor 1440K, and an Ultraviolet (UV) sensor 1440M. Additionally or alternatively, the sensor module 1440 may include an E-nose sensor (not shown), an electromyography (EMG) sensor (not shown), an electroencephalogram (EEG) sensor (not shown), an electrocardiogram (ECG) sensor (not shown), an IR sensor, an iris sensor (not shown), a fingerprint sensor, and the like. The sensor module 1440 may further include a control circuit to control at least one sensor included therein. The sensor module 1440 may be the sensor device 170 shown in FIG. 1.

The input device 1450 may include a touch panel 1452, a (digital) pen sensor 1454, a key 1456, or an ultrasonic input device 1458. The touch panel 1452 may recognize a touch input in at least one method of capacitive, resistive, infrared, and ultrasonic methods. In addition, the touch panel 1452 may further include a control circuit (not shown). In the embodiment of a capacitive method, the touch panel 1452 may recognize physical contact or approach. The touch panel 1452 may further include a tactile layer. In this embodiment, the touch panel 1352 may provide a tactile response to the user.

The (digital) pen sensor 1454 may be implemented in the same or similar method as or to the method of receiving a user's touch input or by using a separate recognition sheet. The key 1456 may include a physical button, an optical key, a keypad, and the like. The ultrasonic input device 1458 identifies data by detecting sound waves through a microphone (for example, the microphone 1488) in the electronic device 1410 through an input device generating ultrasonic signals, and is capable of wireless recognition. According to an embodiment of the present disclosure, the electronic device 1401 may receive a user input from an external device connected thereto (for example, a computer, a server, and the like) by using the communication module 1420.

The display 1460 (e.g., the display 150) may include a panel 1462, a hologram device 1464, or a projector 1466. For example, the panel 1462 may be a Liquid Crystal Display (LCD) or an Active Matrix Organic LED (AM-OLED). For example, the panel 1462 may be implemented to be flexible, transparent, wearable, and the like. The panel 1462 may be configured as a single module along with the touch panel 1452. The hologram device 1464 may show a stereoscopic image in the air using interference of light. The projector 1466 may display an image by projecting light onto a screen. The screen may be located inside or outside of the electronic device 1401. According to an embodiment of the present disclosure, the display 1460 may further include a control circuit to control the panel 1462, the hologram device 1464, or the projector 1466.

The interface 1470 may include an HDMI 1472, a USB 1474, an optical interface 1476, or D-subminiature (D-sub) 1478. The interface 1470 may be included in the communication interface 160 shown in FIG. 1. Additionally or alternatively, the interface 1470 may include a Mobile High Definition Link (MHL) interface, an SD card/Multimedia Card (MMC) interface (not shown) or an Infrared Data Association (IrDA) standard interface (not shown).

The audio module 1480 may convert a sound and an electric signal bidirectionally. For example, at least some elements of the audio module 1480 may be included in the input and output interface 140 shown in FIG. 1. The audio module 1480 may process sound information which is input or output through a speaker 1482, a receiver 1484, an earphone 1486, or a microphone 1488.

The camera module 1491 is a device for photographing a still image and a moving image, and may include one or more image sensors (for example, a front surface sensor or a rear surface sensor), a lens, an Image Signal Processor (ISP) (not shown), or a flash (memory) (for example, an LED or a xenon lamp).

The power management module 1495 may manage power of the electronic device 1401. Although not shown, the power management module 1495 may include a Power Management IC (PMIC), a charging IC, or a battery or fuel gage.

For example, the PMIC may be mounted in an integrated circuit or a SoC semiconductor. The charging method may be divided into a wire charging method and a wireless charging method. The charging IC may charge a battery and may prevent inflow of overvoltage or over current from a charger. According to an embodiment of the present disclosure, the charging IC may include a charging IC for at least one of the wire charging method and the wireless charging method. The wireless charging method may include a magnetic resonance method, a magnetic induction method, or an electromagnetic wave method, and an additional circuit for charging wirelessly, for example, a circuit, such as a coil loop, a resonant circuit, a rectifier, and the like may be added.

For example, the battery gage may measure a remaining battery life of the battery 1496, a voltage, a current, or temperature during charging. The battery 1496 may store or generate electricity and may supply power to the electronic device 1401 by using stored or generated electricity. The battery 1496 may include a rechargeable battery or a solar battery.

The indicator 1497 may display a specific state of the electronic device 1101 or a part of it (for example, the AP 1410), for example, a booting state, a message state, a charging state, and the like. The motor 1498 may convert an electric signal into a mechanical vibration. Although not shown, the electronic device 1401 may include a processing device (for example, a GPU) for supporting a mobile TV. The processing device for supporting the mobile TV may process media data according to standards, such as Digital Multimedia Broadcasting (DMB), Digital Video Broadcasting (DVB), media flow, and the like.

Each of the above-described elements of the electronic device according to various embodiments of the present disclosure may be comprised of one or more components, and the names of the elements may vary according to a kind of the electronic device. The electronic device according to various embodiments of the present disclosure may include at least one of the above-described elements, and some of the elements may be omitted or an additional element may be further included. In addition, some of the elements of the electronic device according to various embodiments of the present disclosure may be combined into a single entity, and may perform the same functions as those of the elements before being combined.

The term "module" used in various embodiments of the present disclosure refers to a unit including one of hardware, software, and firmware, or a combination of two or more of them, for example. For example, the "module" may be used interchangeably with terms like unit, logic, logical block, component or circuit. The "module" may be a minimum unit of an integrally configured component or a part of it. The "module" may be a minimum unit that performs one or more functions or a part of it. The "module" may be implemented mechanically or electronically. For example, the "module" according to various embodiments of the present disclosure may include at least one of an Application Specific Integrated Circuit (ASIC) chip, Field Programmable Gate Arrays (FPGAs), and a programmable logic device which perform any operation that is already well known or will be developed in the future.

According to various embodiments of the present disclosure, at least part of the apparatus (e.g., modules or functions) or method (e.g., operations) of the present disclosure may be implemented by using instructions stored in a computer-readable storage medium in the form of a programming module. When the instructions are executed by one or more processors (e.g., the processor 1410), the one or more processors may perform a function corresponding to the instructions. The computer-readable storage medium may be the memory 1430, for example. At least part of the programming module may be implemented (e.g., executed) by using the processor 210. At least part of the programming module may include a module, a program, a routine, sets of instructions, a process, and the like for performing one or more functions.

Examples of the computer-readable recording medium include magnetic media, such as hard disks, floppy disks and magnetic tapes, optical media, such as Compact Digital ROMs (CD-ROMs) and DVDs, magneto-optical media, such as floptical disks, and hardware devices such as ROMs, RAMs and flash memories that are especially configured to store and execute program commands (e.g., the programming module). Examples of the program commands include machine language codes created by a compiler, and high-level language codes that can be executed by a computer by using an interpreter. The above-described hardware devices may be configured to operate as one or more software modules for performing operations of the present disclosure, and vice versa.

A module or programming module of the present disclosure may include one or more of the above-described elements, may omit some elements, or may further include additional elements. The operations performed by the module, the programming module, or the other elements according to the present disclosure may be performed serially, in parallel, repeatedly, or heuristically. In addition, some operation may be performed in different order or may omitted, and an additional operation may be added.

Figure 15:
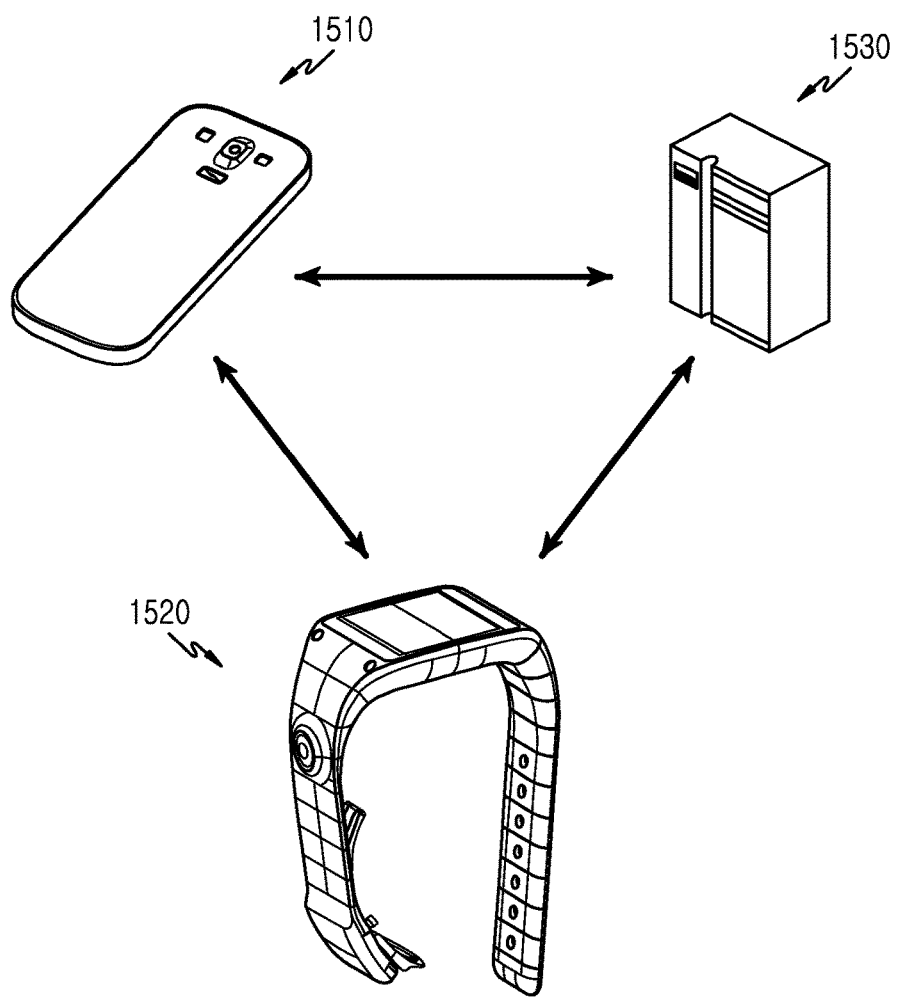
FIG. 15 illustrates a network environment of electronic devices which use a biometric recognition sensor device according to various embodiments of the present disclosure.

FIG. 15 illustrates a network environment of electronic devices which use a biometric recognition sensor device according to various embodiments of the present disclosure. The biometric recognition sensor device according to an embodiment of the present disclosure may be the sensor device 205 shown in FIGS. 2A, 2B, and 2C. A first electronic device 1510 according to an embodiment of the present disclosure may be the electronic device 200 shown in FIGS. 2A, 2B, and 2C.

Referring to FIG. 15, the first electronic device 1510 including at least one biometric recognition sensor may communicate with a second electronic device 1520 and an external server 1530. According to an embodiment of the present disclosure, the biometric recognition sensor may be an HR sensor for measuring a heart rate of a user of the first electronic device 1510. According to an embodiment of the present disclosure, the biometric recognition sensor may be an iris recognition sensor. According to an embodiment of the present disclosure, the biometric recognition sensor may be a fingerprint recognition sensor.

According to an embodiment of the present disclosure, the first electronic device 1510 may acquire biometric recognition information of the device user, and may transmit the acquired biometric recognition information to the second electronic device 1520 or the external server 1530. According to an embodiment of the present disclosure, the second electronic device 1520 may be an electronic device which interworks with the first electronic device 1510 or may be an auxiliary electronic device. According to an embodiment of the present disclosure, the second electronic device 1520 may be a wearable electronic device which interworks with the first electronic device 1510. According to an embodiment of the present disclosure, the second electronic device 1520 may be an electronic device similar to the first electronic device 1510. According to an embodiment of the present disclosure, the second electronic device 1520 may operate solely or may operate by interworking with the first electronic device 1510.

According to various embodiments of the present disclosure, the external server 1530 may be a server of a medical institution or a server for health care. The external server 1530 may receive biometric recognition information provided from the first electronic device 1510 or the second electronic device 1520 and may provide a corresponding medical service or corresponding health care information to the first electronic device 1510 or the second electronic device 1520 based on the received biometric recognition information.

Figure 16:
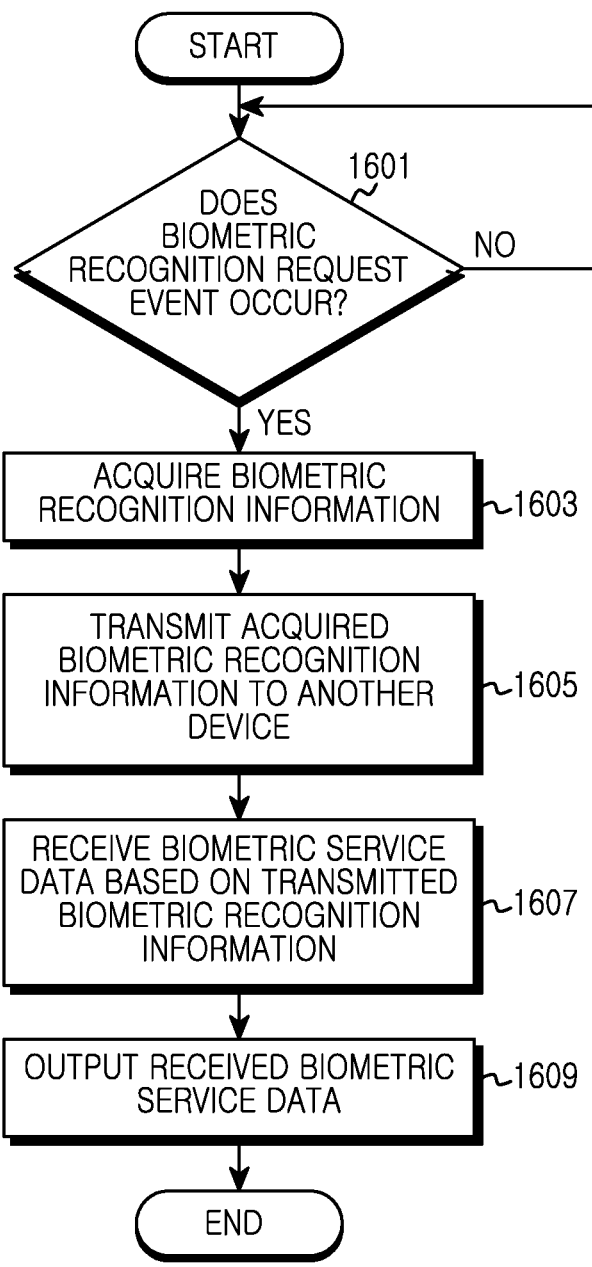
FIG. 16 is a flowchart illustrating a method of an electronic device having a biometric recognition sensor device according to various embodiments of the present disclosure.

FIG. 16 is a flowchart illustrating a method of an electronic device having a biometric recognition sensor device according to various embodiments of the present disclosure.

Referring to FIG. 16, the electronic device may determine whether a biometric recognition request event occurs or not in operation 1601. According to an embodiment of the present disclosure, the electronic device may identify the biometric recognition request event based on a user's key input. According to an embodiment of the present disclosure, the electronic device may determine whether a biometric recognition request event of another electronic device or a medical institution occurs.

When the biometric recognition request event occurs, the electronic device may acquire biometric recognition information in operation 1603. According to an embodiment of the present disclosure, when the biometric recognition sensor is an HR sensor, the electronic device may acquire a heart rate or related information based on the user's finger brought into contact with the HR sensor, as shown in the above-described drawings.

In operation 1605, the electronic device may transmit the biometric recognition information acquired by the biometric recognition sensor to another device, and, in operation 1607, the electronic device may receive biometric service data based on the transmitted biometric recognition information. According to an embodiment of the present disclosure, another device may be a server of a medical institution or an external server for health care. For example, the server of the medical institution may analyze the HR information acquired from the electronic device, identify a user's health state, and transmit related information to the electronic device.

In operation 1609, the electronic device may output the received biometric service data. According to an embodiment of the present disclosure, the electronic device may visually output the biometric service data received from another device. According to an embodiment of the present disclosure, the electronic device may output the biometric service data through a display provided in the electronic device.

According to an embodiment of the present disclosure, the electronic device may audibly output the biometric service data received from another device. According to an embodiment of the present disclosure, the electronic device may output the biometric service data through a speaker device provided in the electronic device.

According to an embodiment of the present disclosure, the electronic device may actually output the biometric service data received from another device. According to an embodiment of the present disclosure, the electronic device may output the biometric service data through a vibrator motor, a haptic sensor, and the like provided in the electronic device.

According to an embodiment of the present disclosure, the electronic device may output the received biometric service data in various output methods such that the user of the electronic device can recognize the biometric service data.

According to various embodiments of the present disclosure, user's convenience can be improved by applying at least one biometric recognition sensor device at an appropriate location of the electronic device. In addition, for example, the electronic device can accommodate at least one electronic component along with the sensor device, thereby reducing a manufacturing cost, can overcome a design limit by reducing a mounting space and can improve the appearance of the electronic device for aesthetic purpose.

Certain aspects of the present disclosure can also be embodied as computer readable code on a non-transitory computer readable recording medium. A non-transitory computer readable recording medium is any data storage device that can store data which can be thereafter read by a computer system. Examples of the non-transitory computer readable recording medium include Read-Only Memory (ROM), Random-Access Memory (RAM), Compact Disc-ROMs (CD-ROMs), magnetic tapes, floppy disks, and optical data storage devices. The non-transitory computer readable recording medium can also be distributed over network coupled computer systems so that the computer readable code is stored and executed in a distributed fashion. In addition, functional programs, code, and code segments for accomplishing the present disclosure can be easily construed by programmers skilled in the art to which the present disclosure pertains.

At this point it should be noted that the various embodiments of the present disclosure as described above typically involve the processing of input data and the generation of output data to some extent. This input data processing and output data generation may be implemented in hardware or software in combination with hardware. For example, specific electronic components may be employed in a mobile device or similar or related circuitry for implementing the functions associated with the various embodiments of the present disclosure as described above. Alternatively, one or more processors operating in accordance with stored instructions may implement the functions associated with the various embodiments of the present disclosure as described above. If such is the case, it is within the scope of the present disclosure that such instructions may be stored on one or more non-transitory processor readable mediums. Examples of the processor readable mediums include a ROM, a RAM, CD-ROMs, magnetic tapes, floppy disks, and optical data storage devices. The processor readable mediums can also be distributed over network coupled computer systems so that the instructions are stored and executed in a distributed fashion. In addition, functional computer programs, instructions, and instruction segments for accomplishing the present disclosure can be easily construed by programmers skilled in the art to which the present disclosure pertains.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A mobile electronic device comprising:
   at least one processor;
   a display electrically connected with the at least one processor;
   a transceiver electrically connected with the at least one processor;
   a housing for housing at least a part of the display, the at least one processor, and the transceiver;
   a heart rate (HR) sensor positioned on one surface of the housing, electrically connected with the at least one processor, and including at least one part that is externally exposed;
   at least one electronic component exposed through a part of the housing; and
   an integral window for covering the HR sensor and the at least one electronic component,
   wherein the integral window includes:
      a first member formed of a transparent material, and
      a second member including at least one penetrating hole,
   wherein the first member includes a top portion disposed on one surface of the second member, a bottom portion disposed under other surface of the second member, and at least one connection portion penetrating through the at least one penetrating hole for connecting the top portion and the bottom portion, and
   wherein, the at least one processor is configured to:
      control the HR sensor to measure biometric recognition information upon receiving a request, based on a user's input, for the biometric recognition information from the mobile electronic device or another device,
      control the transceiver to transmit the measured biometric recognition information to the other device,
      control the transceiver to receive, from the other device, biometric service data based on the transmitted measured biometric recognition information, and
      output the received biometric service data to the display.

2. The mobile electronic device of claim 1, wherein the HR sensor is comprised in a second surface of the housing opposite to a first surface of the housing which comprises the display.

3. The mobile electronic device of claim 2, wherein the second surface of the housing comprises:
   a first side;
   a second side which is longer than the first side and is perpendicular to the first side;
   a third side which has a same length as that of the first side and is parallel to the first side; and
   a fourth side which has a same length as that of the second side and is parallel to the second side,
   wherein the HR sensor is located between an imaginary line which crosses over a ⅓ point of the length of the second side from the first side, and the first side.

4. The mobile electronic device of claim 1, further comprising:
   a camera externally exposed through a part of the housing, and
   wherein the HR sensor is positioned adjacent to the camera.

5. The mobile electronic device of claim 1,
   wherein the HR sensor comprises a window, at least a part of the window is transparent, and
   wherein a top surface of the window:
      does not protrude further than at least one of a surface of a portion of the housing or a surface of the portion surrounding the HR sensor, or
      is located in a dent formed from a surface of the housing.

6. The mobile electronic device of claim 1,
   wherein the HR sensor comprises a window at least a part of which is transparent, and
   wherein a top surface of the window:
      does not protrude further than at least one of a surface of a portion of a decoration member or a surface of the portion surrounding the HR sensor, or
      is located in a dent formed from a surface of the decoration member.

7. The mobile electronic device of claim 1, wherein the electronic component comprises a light emitting diode (LED).

8. The mobile electronic device of claim 1,
   wherein the second member is interposed between the top portion and the bottom portion and formed of an opaque material,
   wherein the top portion, the bottom portion, and the connecting portion are integrally formed with one another, and
   wherein the connecting portion of the first member penetrates through the penetrating hole, and is in contact with an inner wall of the penetrating hole.

9. The mobile electronic device of claim 1, wherein the integral window includes an opaque material except for an HR sensor area and an area of the electronic component.

10. The mobile electronic device of claim 1, wherein the electronic component comprises a flash light emitting diode (LED).

11. The mobile electronic device of claim 1, wherein the bottom portion is covered with an area under which the HR sensor is disposed apart from the bottom portion by a distance.

12. The mobile electronic device of claim 1, wherein the penetrating hole is disposed on an area that corresponds to the HR sensor.

* * * * *